(12) United States Patent
Harris et al.

(10) Patent No.: US 11,179,154 B2
(45) Date of Patent: Nov. 23, 2021

(54) SURGICAL STAPLING END EFFECTOR COMPONENT WITH DEFORMABLE TIP SKEWING IN MULTIPLE PLANES

(71) Applicant: ETHICON LLC, Guaynabo, PR (US)

(72) Inventors: Jason L. Harris, Lebanon, OH (US); Gregory J. Bakos, Mason, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 162 days.

(21) Appl. No.: 16/035,821

(22) Filed: Jul. 16, 2018

(65) Prior Publication Data

US 2020/0015812 A1 Jan. 16, 2020

(51) Int. Cl.
*A61B 17/072* (2006.01)
*A61B 17/28* (2006.01)
(Continued)

(52) U.S. Cl.
CPC .......... *A61B 17/072* (2013.01); *A61B 17/282* (2013.01); *A61B 17/2909* (2013.01);
(Continued)

(58) Field of Classification Search
CPC . A61B 17/072; A61B 17/282; A61B 17/2909; A61B 2017/2909;
(Continued)

(56) References Cited

U.S. PATENT DOCUMENTS 4,392,827 A * 7/1983 Martin ..................... A61C 5/50
433/224
4,805,823 A 2/1989 Rothfuss
(Continued)

FOREIGN PATENT DOCUMENTS

CN 209 269 768 U 8/2019
EP 2 380 503 A1 10/2011
(Continued)

OTHER PUBLICATIONS

European Search Report, Extended, and Written Opinion dated Mar. 20, 2020 for Application No. EP 19186272.1, 13 pgs.
(Continued)

*Primary Examiner* — Thanh K Truong
*Assistant Examiner* — Scott A Howell
(74) *Attorney, Agent, or Firm* — Frost Brown Todd LLC

(57) ABSTRACT

An instrument includes a body, a shaft extending from the body, and an end effector in communication with the shaft. The end effector defines a longitudinal axis. The end effector includes first and second opposing jaws, a staple cartridge, and a placement tip. At least one of the first and second jaws is movable relative to the other of the first and second jaws between an open configuration and a closed configuration. The staple cartridge is coupled with the second jaw. The placement tip extends from a distal end of the first jaw or a distal end of the second jaw. The placement tip extends along a curvilinear path and terminates at a tip end. Successive perimeters of the placement tip taken perpendicular to the curvilinear path decrease moving toward the tip end. The tip end extends at an angle relative to the longitudinal axis of the end effector.

19 Claims, 17 Drawing Sheets

(51) Int. Cl.
*A61B 17/29* (2006.01)
*A61B 17/064* (2006.01)

(52) U.S. Cl.
CPC .......... *A61B 2017/0645* (2013.01); *A61B 2017/07221* (2013.01); *A61B 2017/07257* (2013.01); *A61B 2017/07271* (2013.01); *A61B 2017/07285* (2013.01); *A61B 2017/2913* (2013.01); *A61B 2017/2926* (2013.01); *A61B 2017/2946* (2013.01)

(58) Field of Classification Search
CPC .. A61B 2017/0645; A61B 2017/07221; A61B 2017/07257; A61B 2017/07271; A61B 2017/07285; A61B 2017/2913; A61B 2017/2926; A61B 2017/2946
See application file for complete search history.

(56) References Cited

U.S. PATENT DOCUMENTS

| | | | | |
|---|---|---|---|---|
| 4,959,067 | A * | 9/1990 | Muller | A61B 17/00 600/201 |
| 5,014,899 | A | 5/1991 | Presty et al. | |
| 5,415,334 | A | 5/1995 | Williamson et al. | |
| 5,465,895 | A | 11/1995 | Knodel et al. | |
| 5,597,107 | A | 1/1997 | Knodel et al. | |
| 5,632,432 | A | 5/1997 | Schulze et al. | |
| 5,673,840 | A | 10/1997 | Schulze et al. | |
| 5,704,534 | A | 1/1998 | Huitma et al. | |
| 5,792,135 | A | 8/1998 | Madhani et al. | |
| 5,814,055 | A | 9/1998 | Knodel et al. | |
| 5,817,084 | A | 10/1998 | Jensen | |
| 5,865,361 | A * | 2/1999 | Milliman | A61B 17/07207 227/176.1 |
| 5,878,193 | A | 3/1999 | Wang et al. | |
| 6,231,565 | B1 | 5/2001 | Tovey et al. | |
| 6,270,343 | B1 * | 8/2001 | Martin | A61C 5/50 433/32 |
| 6,364,888 | B1 | 4/2002 | Niemeyer et al. | |
| 6,755,815 | B2 * | 6/2004 | Schultz | A61B 17/00234 606/1 |
| 6,783,524 | B2 | 8/2004 | Anderson et al. | |
| 6,978,921 | B2 | 12/2005 | Shelton et al. | |
| 7,000,818 | B2 | 2/2006 | Shelton et al. | |
| 7,143,923 | B2 | 12/2006 | Shelton et al. | |
| 7,303,108 | B2 | 12/2007 | Shelton | |
| 7,367,485 | B2 | 5/2008 | Shelton et al. | |
| 7,380,695 | B2 | 6/2008 | Doll et al. | |
| 7,380,696 | B2 | 6/2008 | Shelton et al. | |
| 7,404,508 | B2 | 7/2008 | Smith et al. | |
| 7,434,715 | B2 | 10/2008 | Shelton et al. | |
| 7,434,717 | B2 * | 10/2008 | Shelton, IV | A61B 17/105 227/176.1 |
| 7,524,320 | B2 | 4/2009 | Tierney et al. | |
| 7,644,848 | B2 | 1/2010 | Swayze et al. | |
| 7,691,098 | B2 | 4/2010 | Wallace et al. | |
| 7,721,930 | B2 | 5/2010 | McKenna et al. | |
| 7,806,891 | B2 | 10/2010 | Nowlin et al. | |
| 8,066,166 | B2 * | 11/2011 | Demmy | A61B 17/07207 227/175.1 |
| 8,136,711 | B2 * | 3/2012 | Beardsley | A61B 17/07207 227/175.1 |
| 8,210,411 | B2 | 7/2012 | Yates et al. | |
| 8,348,123 | B2 | 1/2013 | Scirica et al. | |
| 8,403,195 | B2 | 3/2013 | Beardsly et al. | |
| 8,403,196 | B2 * | 3/2013 | Beardsley | A61B 17/07207 227/175.1 |
| 8,408,439 | B2 | 4/2013 | Huang et al. | |
| 8,453,914 | B2 | 6/2013 | Laurent et al. | |
| 8,479,969 | B2 | 7/2013 | Shelton | |
| 8,496,153 | B2 * | 7/2013 | Demmy | A61B 17/07207 227/175.1 |
| 8,573,461 | B2 | 11/2013 | Shelton et al. | |
| 8,573,465 | B2 | 11/2013 | Shelton | |
| 8,602,288 | B2 | 12/2013 | Shelton et al. | |
| 8,616,431 | B2 | 12/2013 | Timm et al. | |
| 8,690,039 | B2 | 4/2014 | Beardsly et al. | |
| 8,714,429 | B2 | 5/2014 | Demmy | |
| 8,783,541 | B2 | 7/2014 | Shelton et al. | |
| 8,800,838 | B2 | 8/2014 | Shelton | |
| 8,820,605 | B2 | 9/2014 | Shelton | |
| 8,844,789 | B2 | 9/2014 | Shelton et al. | |
| 8,844,790 | B2 | 9/2014 | Demmy et al. | |
| 9,016,546 | B2 | 4/2015 | Demmy et al. | |
| 9,039,736 | B2 | 5/2015 | Scirica et al. | |
| 9,186,142 | B2 | 11/2015 | Fanelli et al. | |
| 9,301,759 | B2 | 4/2016 | Spivey et al. | |
| 9,433,416 | B2 | 9/2016 | Beardsly et al. | |
| 9,517,065 | B2 * | 12/2016 | Simms | A61B 17/07207 |
| 9,522,004 | B2 | 12/2016 | Demmy | |
| 9,597,078 | B2 * | 3/2017 | Scirica | A61B 17/07207 |
| 9,622,746 | B2 * | 4/2017 | Simms | A61B 17/07207 |
| 9,713,470 | B2 | 7/2017 | Scirica et al. | |
| 9,717,497 | B2 | 8/2017 | Zerkle et al. | |
| 9,795,379 | B2 | 10/2017 | Leimbach et al. | |
| 9,808,248 | B2 | 11/2017 | Hoffman | |
| 9,839,421 | B2 | 12/2017 | Zerkle et al. | |
| 9,913,642 | B2 | 3/2018 | Leimbach et al. | |
| 9,936,952 | B2 * | 4/2018 | Demmy | A61B 17/07207 |
| 9,936,968 | B2 | 4/2018 | Demmy et al. | |
| 9,943,311 | B2 | 4/2018 | Scirica et al. | |
| 10,080,564 | B2 | 9/2018 | Beardsly et al. | |
| 10,166,023 | B2 | 1/2019 | Vendely et al. | |
| 2004/0243151 | A1 | 12/2004 | Demmy et al. | |
| 2005/0119669 | A1 * | 6/2005 | Demmy | A61B 17/068 606/139 |
| 2005/0216055 | A1 | 9/2005 | Scirica et al. | |
| 2006/0041274 | A1 * | 2/2006 | Su | A61B 17/29 606/205 |
| 2014/0166723 | A1 | 6/2014 | Beardsly et al. | |
| 2014/0239036 | A1 | 8/2014 | Zerkle et al. | |
| 2014/0239037 | A1 | 8/2014 | Boudreaux et al. | |
| 2014/0239038 | A1 | 8/2014 | Leimbach et al. | |
| 2014/0239041 | A1 | 8/2014 | Zerkle | |
| 2014/0239043 | A1 | 8/2014 | Simms et al. | |
| 2014/0239044 | A1 | 8/2014 | Hoffman | |
| 2014/0263555 | A1 * | 9/2014 | Hufnagel | A61B 17/00234 227/176.1 |
| 2015/0173752 | A1 | 6/2015 | Demmy et al. | |
| 2015/0272575 | A1 | 10/2015 | Leimbach et al. | |
| 2015/0282809 | A1 | 10/2015 | Shelton, IV et al. | |
| 2016/0143659 | A1 | 5/2016 | Glutz et al. | |
| 2016/0278774 | A1 | 9/2016 | Shelton, IV et al. | |
| 2017/0055981 | A1 | 3/2017 | Vendely et al. | |
| 2017/0086823 | A1 | 3/2017 | Leimbach et al. | |
| 2017/0105731 | A1 * | 4/2017 | Scheib | A61B 17/068 |
| 2018/0235609 | A1 | 8/2018 | Harris et al. | |
| 2018/0235610 | A1 | 8/2018 | Harris et al. | |
| 2018/0235611 | A1 | 8/2018 | Harris et al. | |
| 2018/0235619 | A1 | 8/2018 | Harris et al. | |
| 2018/0325514 | A1 | 11/2018 | Harris et al. | |
| 2018/0325515 | A1 | 11/2018 | Harris et al. | |
| 2018/0325516 | A1 | 11/2018 | Harris et al. | |
| 2019/0076143 | A1 * | 3/2019 | Smith | A61B 34/37 |

FOREIGN PATENT DOCUMENTS

| | | |
|---|---|---|
| EP | 2772202 | 9/2014 |
| EP | 2 913 010 A2 | 9/2015 |
| EP | 3 420 936 A1 | 1/2019 |
| WO | WO 94/05217 A1 | 3/1994 |
| WO | WO 2004/096057 | 11/2004 |
| WO | WO 2013/151888 A1 | 10/2013 |
| WO | WO 2015/153324 A1 | 10/2015 |
| WO | WO 2017/083129 | 5/2017 |

OTHER PUBLICATIONS

International Search Report and Written Opinion dated Mar. 19, 2020 for Application No. PCT/IB2019/056069, 18 pgs.

(56) References Cited

OTHER PUBLICATIONS

European Search Report dated Aug. 7, 2018 for Application No. 18157228.0, 8 pages.
International Search Report and Written Opinion dated Apr. 19, 2018 for International Application No. PCT/US2018/017551, 17 pages.
U.S. Appl. No. 60/466,378, filed Aug. 29, 2003.
U.S. Appl. No. 60/843,254, filed Sep. 8, 2006.
U.S. Appl. No. 11/851,495, filed Sep. 7, 2007.
U.S. Appl. No. 14/868,718, filed Sep. 29, 2015.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
U.S. Appl. No. 16/035,803, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,865, filed Jul. 16, 2018.
U.S. Appl. No. 16/035,872, filed Jul. 16, 2018.
Design U.S. Appl. No. 29/594,332, filed Feb. 17, 2017.
Design U.S. Appl. No. 29/594,335, filed Feb. 17, 2017.
Deisgn U.S. Appl. No. 29/594,340, filed Feb. 17, 2017.

* cited by examiner

SURGICAL STAPLING END EFFECTOR COMPONENT WITH DEFORMABLE TIP SKEWING IN MULTIPLE PLANES

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
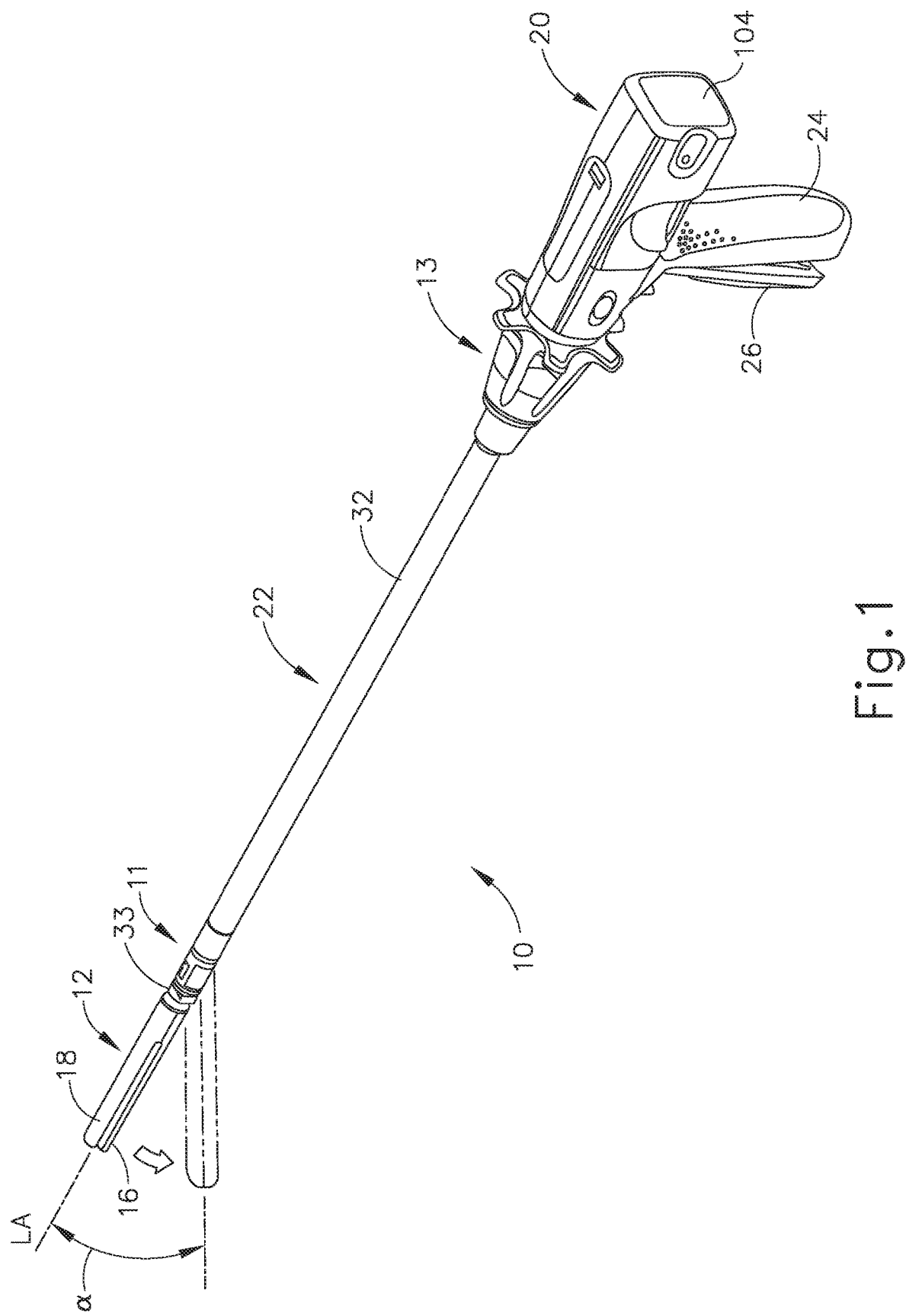
FIG. 1 depicts a perspective view of a first exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. FIRST EXEMPLARY SURGICAL INSTRUMENT HAVING A FIRST EXEMPLARY END EFFECTOR

FIGS. 1-7 depict a first exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with a first exemplary end effector (12). Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). Articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

End effector (12) of the present example includes a lower jaw (16) and a pivotable anvil (18). Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
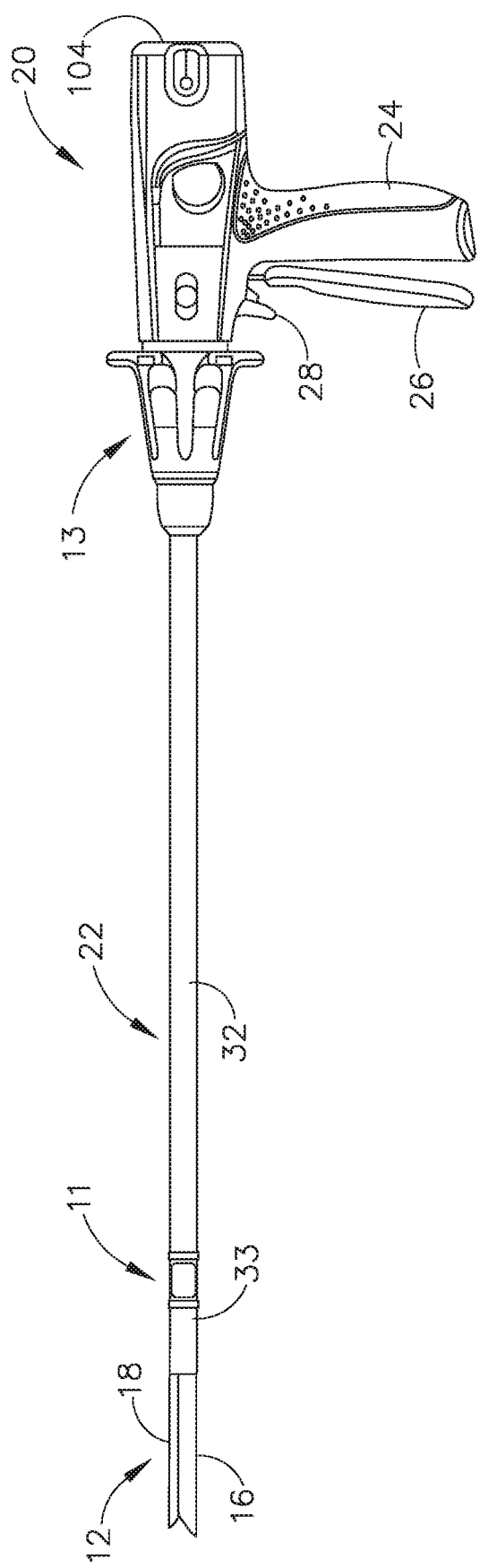
FIG. 2 depicts a side view of the instrument of FIG. 1 with a first exemplary end effector.

Handle portion (20) also includes a firing trigger (28) (shown in FIG. 2). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

FIGS. 3-6 depict end effector (12) employing an E-beam form of firing beam (14). As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein.

Figure 3:
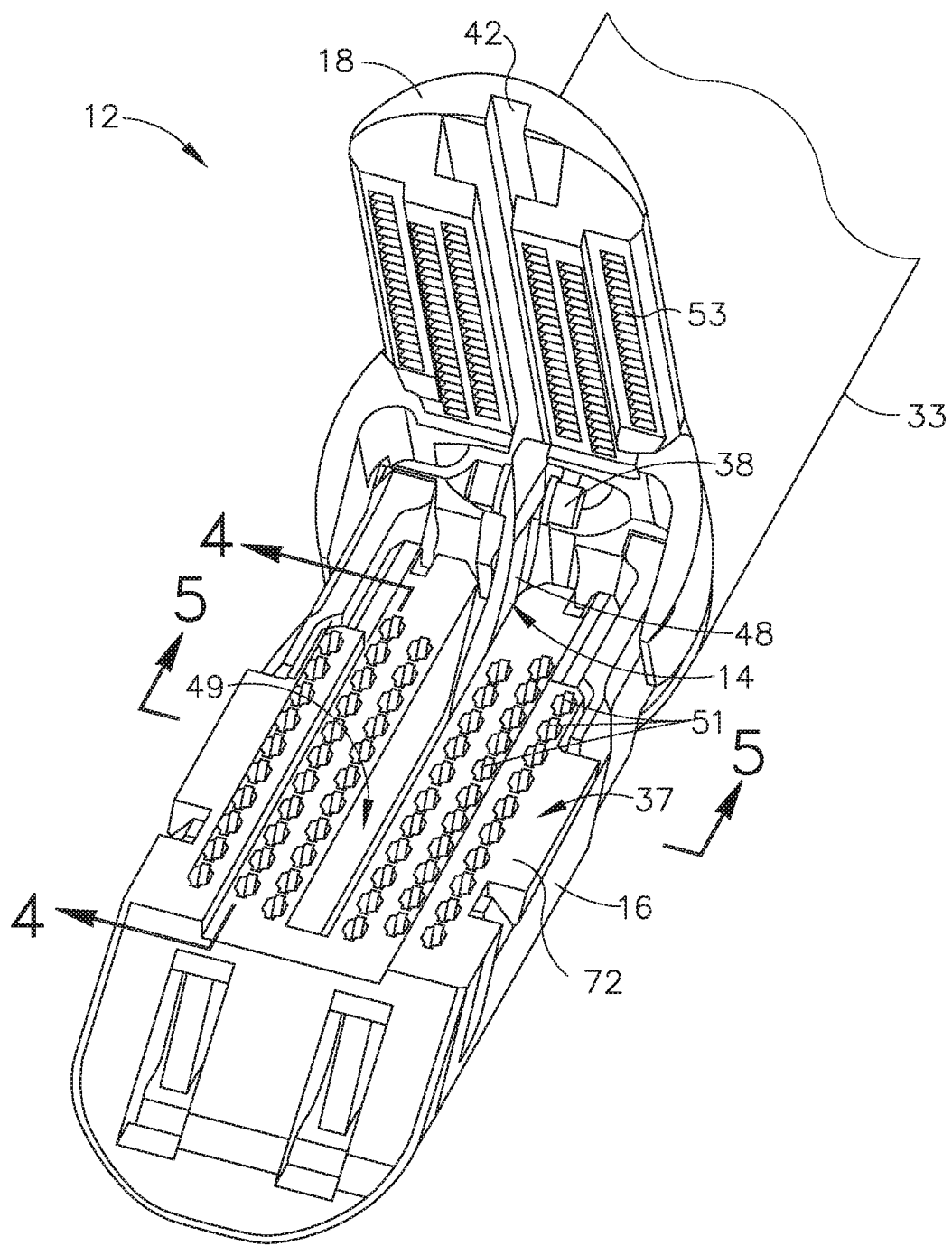
FIG. 3 depicts a perspective view of the end effector of the instrument of FIG. 1 in an open configuration.
Figure 4A:
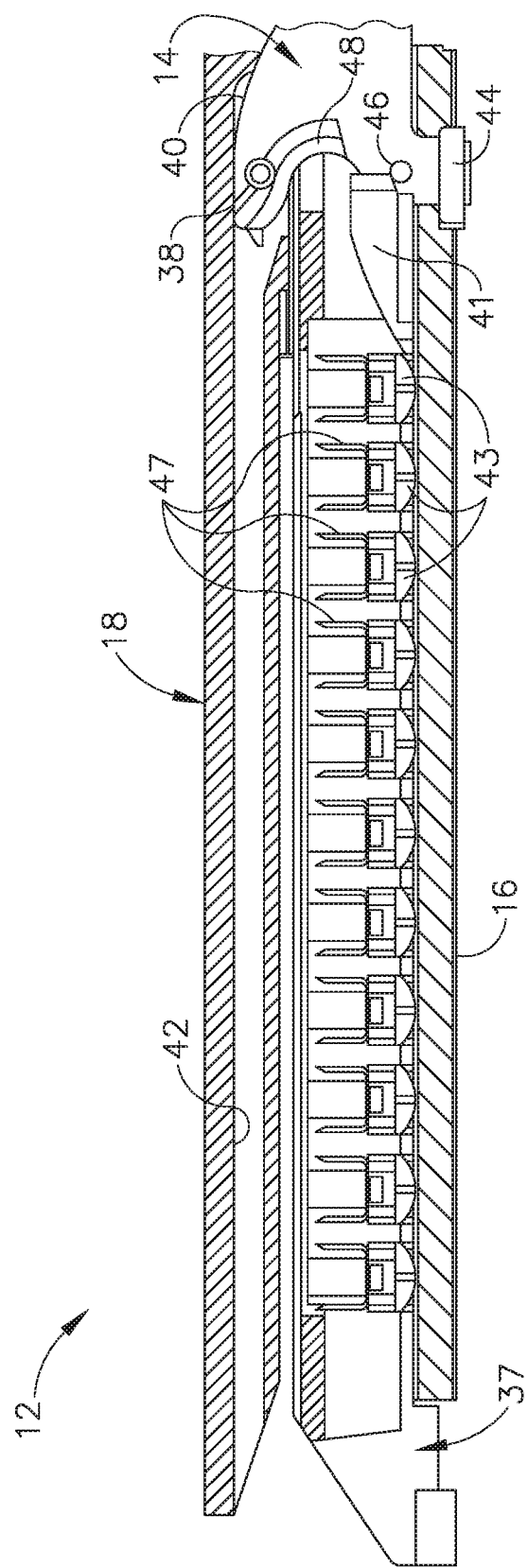
FIG. 4A depicts a side cross-sectional view of the end effector of FIG. 3, taken along line 4-4 of FIG. 3, with the firing beam in a proximal position.
Figure 4B:
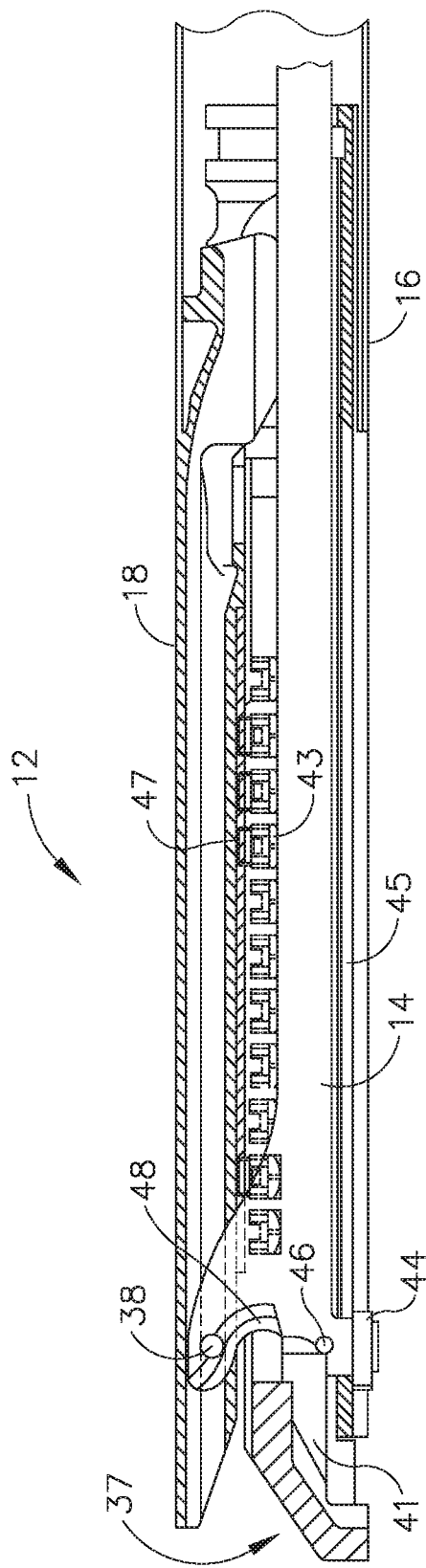
FIG. 4B depicts a side cross-sectional view of the end effector of FIG. 3, taken along line 4-4 of FIG. 3, with the firing beam in a distal position.
Figure 5:
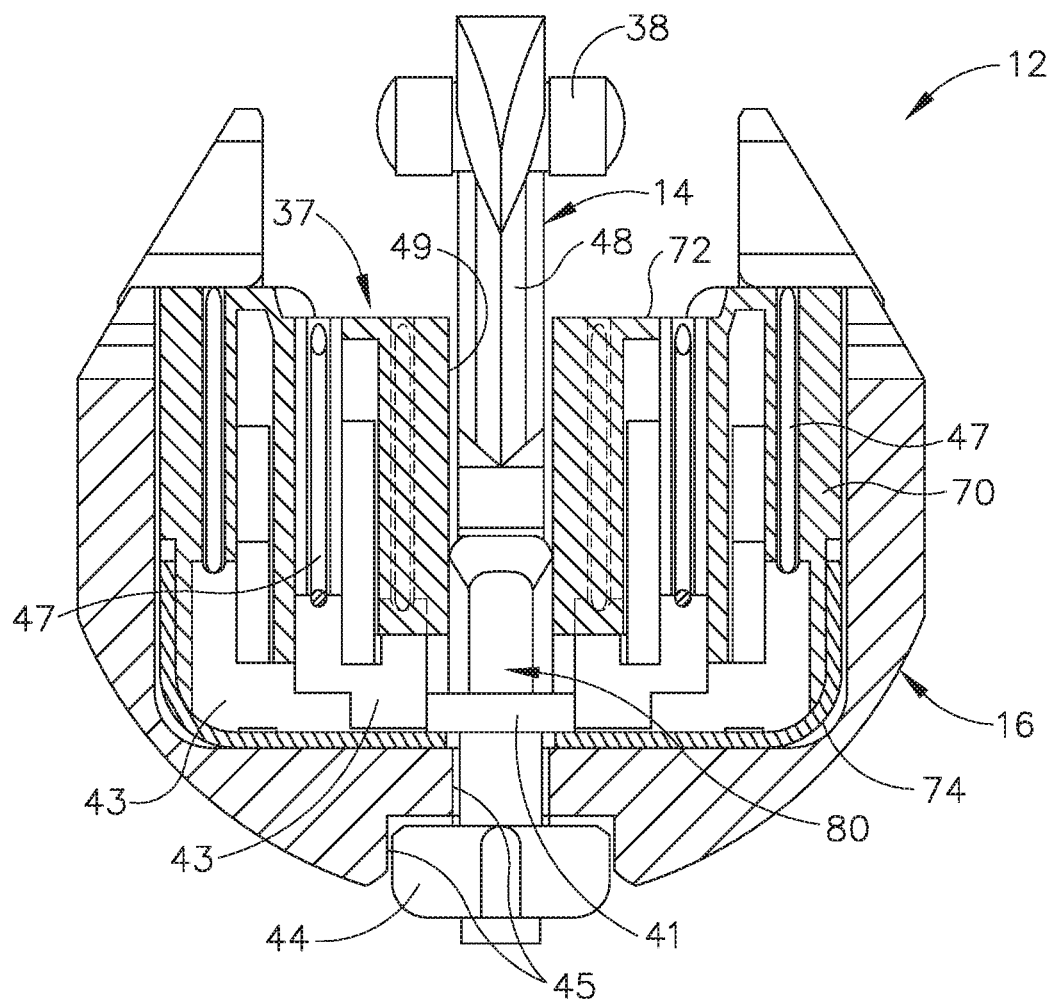
FIG. 5 depicts an end cross-sectional view of the end effector of FIG. 3, taken along line 5-5 of FIG. 3.
Figure 6:
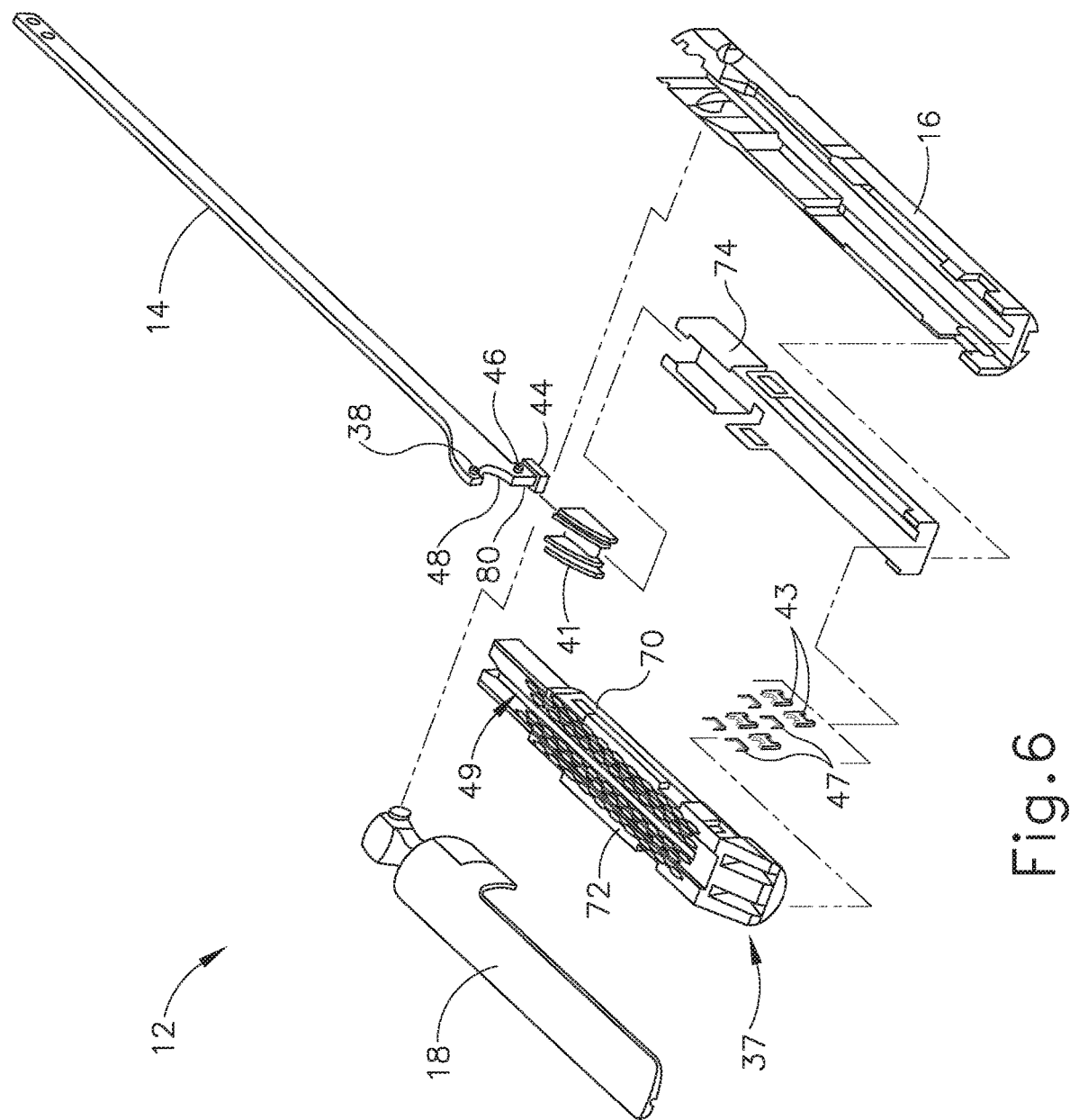
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37). Staple cartridge (37) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and pushes wedge sled (41) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B; but are shown in FIG. 3. Anvil (18) is intentionally omitted from the view in FIG. 5.

Figure 7:
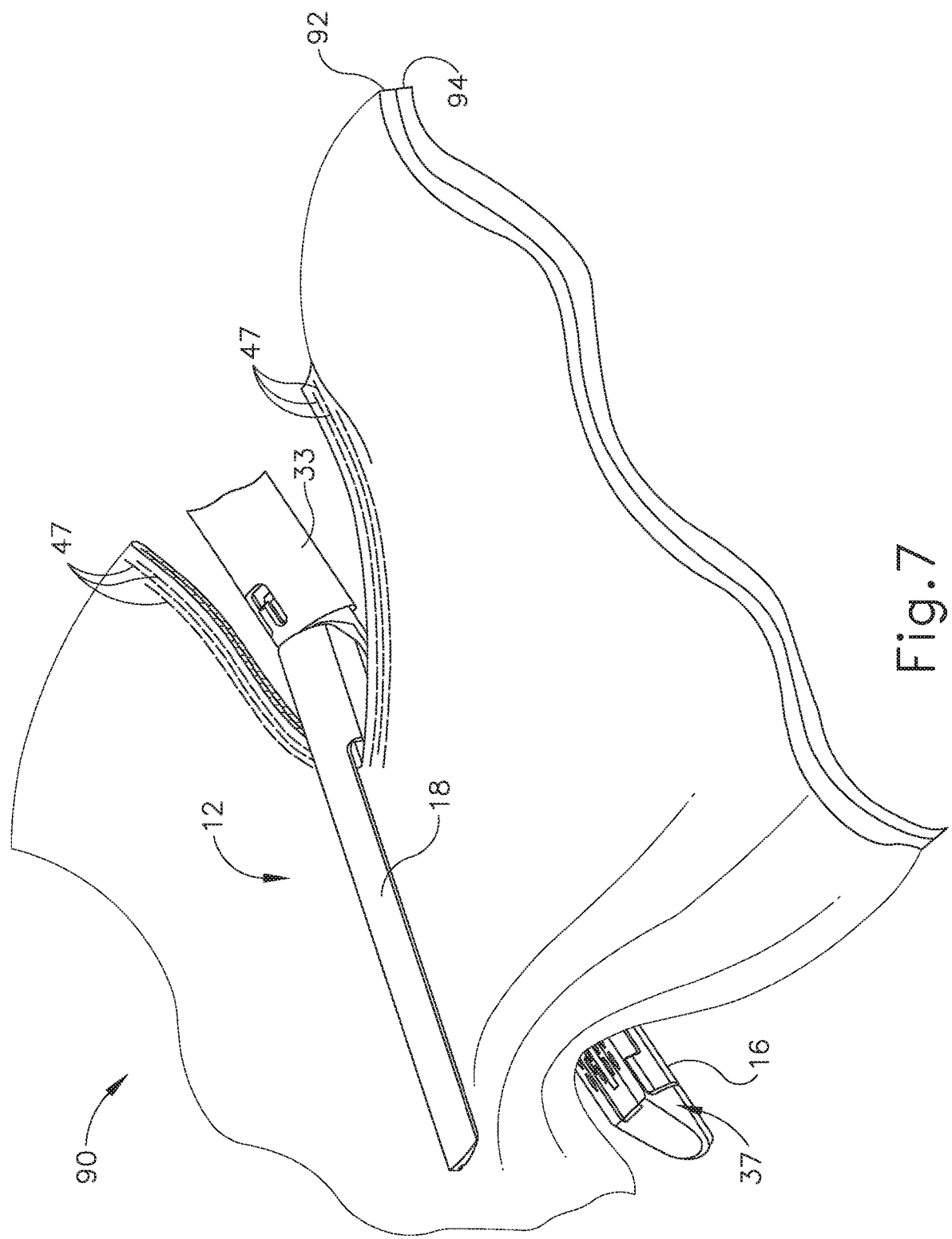
FIG. 7 depicts a perspective view of the end effector of FIG. 3, positioned at tissue and having been actuated once in the tissue.

FIG. 7 shows end effector (12) having been actuated through a single stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). End effector (12) is withdrawn from the patient after the first stroke is complete, spent staple cartridge (37) is replaced with a new staple cartridge, and end effector (12) is then again inserted to reach the stapling site for further cutting and stapling. This process may be repeated until the desired number of cuts and staples (47) have been provided.

Some versions of instrument (10) provide motorized control of firing beam (14). Such motorized control may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein; and/or U.S. Pat. No. 8,210,411, entitled "Motor-Driven Surgical Instrument," issued Jul. 3, 2012, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition, or in the alternative, the pivot axis may slide along the slot/channel first, with anvil (18) then pivoting about the pivot axis after the pivot axis has slid a certain distance along the slot/channel. Such sliding/translating pivotal movement is encompassed within terms such as "pivot," "pivots," "pivotal," "pivotable," "pivoting," and the like.

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. FIRST EXEMPLARY SURGICAL INSTRUMENT HAVING A SECOND EXEMPLARY END EFFECTOR

As end effector (12) is inserted into a surgical site, the user may rotate shaft (22) and end effector (12) of instrument (10) during the procedure. In some instances, lower jaw (16) of end effector (12) is visible rather than anvil (18); while in other instances anvil (18) is visible rather than lower jaw (16). It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely encompass the vessel to be cut, such that the vessel may be fully cut and stapled in one single actuation. It may be desirable to enable the operator to more easily visually confirm proper position of anvil (18) and lower jaw (16) in relation to a vessel to fully clamp the vessel. One potential way of enhancing visualization of the surgical site may include improving visualization of the area adjacent to the distal tip of lower jaw (16) and anvil (18). It may also be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
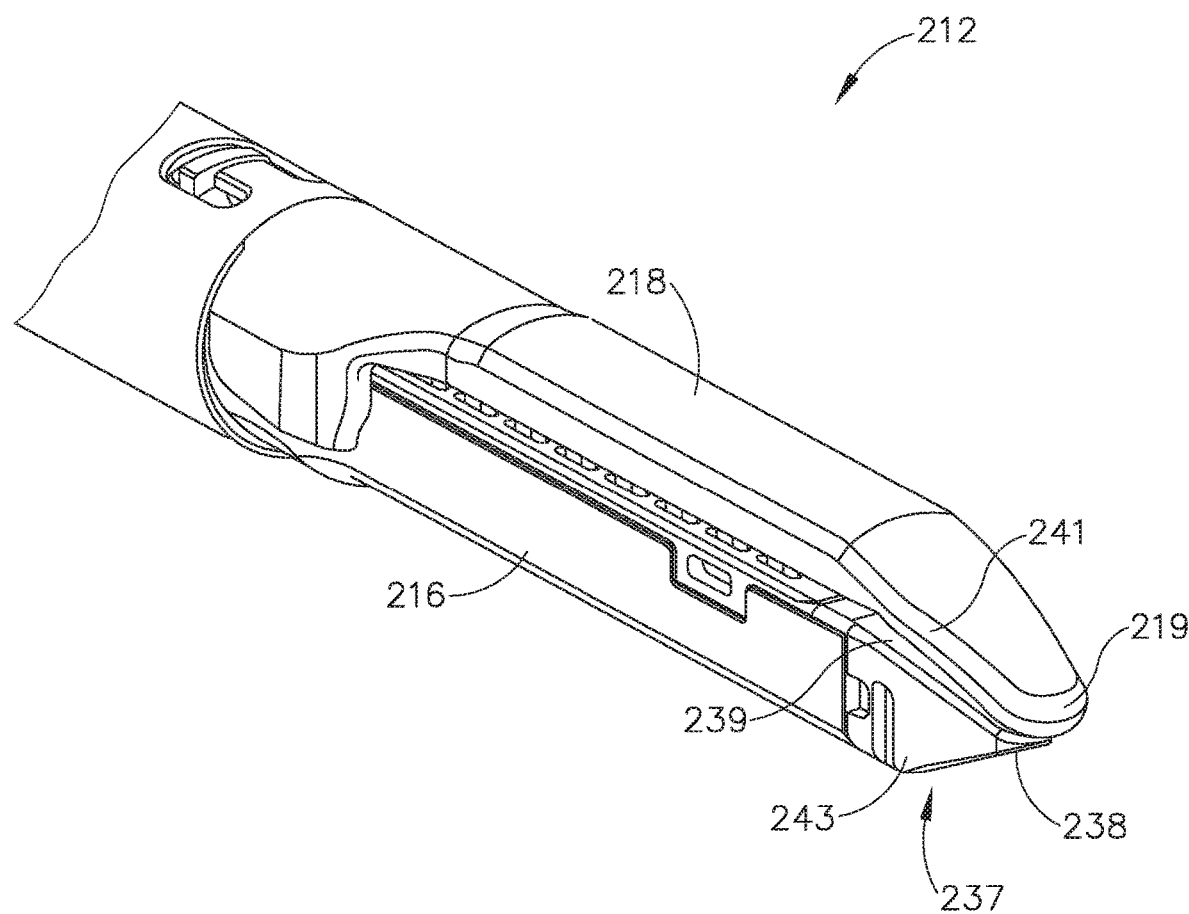
FIG. 8 depicts a perspective view of a second exemplary end effector that includes an angled cartridge and an angled anvil with a tip.

FIG. 8 depicts a second exemplary end effector (212) comprising an anvil (218) and a lower jaw (216). End effector (212) may be used in place of end effector (12) of instrument (10). End effector (212) may be integrally formed with instrument (10) or, in the alternative, may be interchangeable with end effector (12) of instrument (10). Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
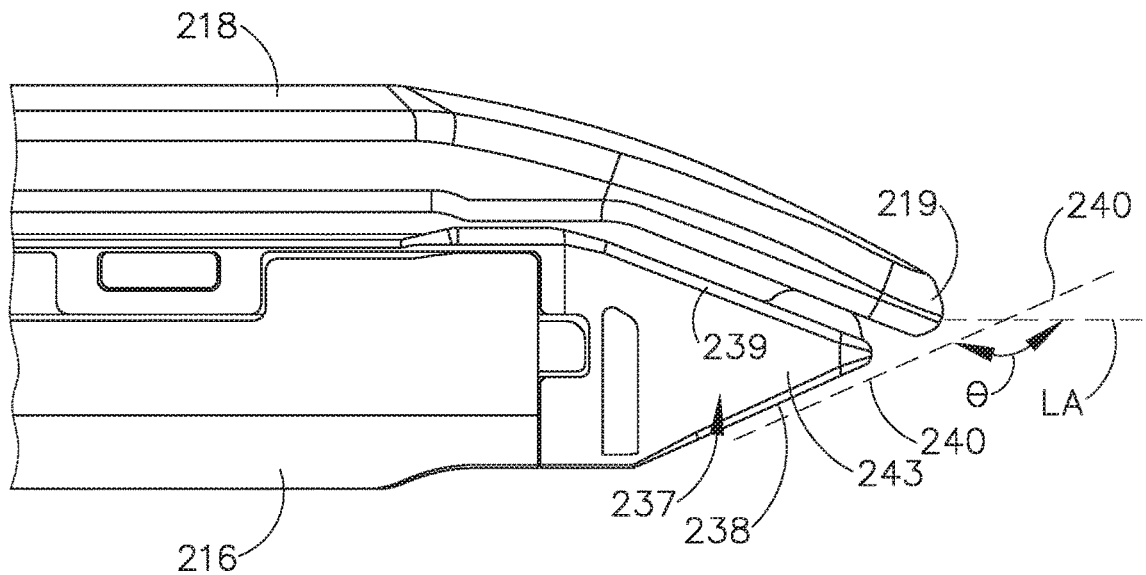
FIG. 9 depicts an enlarged side view of the end effector of FIG. 8.
Figure 10:
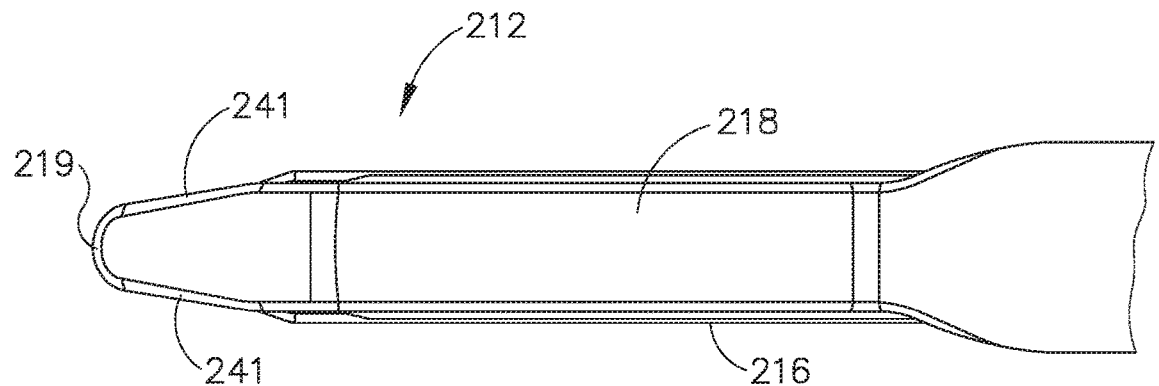
FIG. 10 depicts an enlarged top view of the end effector of FIG. 8.

Anvil (218) as shown in FIGS. 8-10 has an elongated shape where the distal portion of anvil (218) angles toward cartridge (237) such that the distal most tip (219) of anvil (218) extends distally longitudinally further than cartridge (237). Alternatively, distal most tip (219) may extend to a distance longitudinally equal to cartridge (237) or proximal relative to the distal most point on cartridge (237). As seen best in FIG. 10, anvil (218) includes sides (241) that taper laterally as they approach the distal most tip (219) of anvil (218). The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site.

Cartridge (237) is operable to hold staples like staples (47) shown in FIG. 4A for driving into tissue. As shown in FIG. 9, the distal end of cartridge (237) has a triangular profile defined by an upper tapered surface (239) and a lower tapered surface (238). The distal end of cartridge (237) also comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). Sight line (240) intersects longitudinal axis (LA), which extends longitudinally through end effector (212), to form a viewing angle (θ).

The planar shape of lower tapered surface (238) facilitate visualization of the distal most tip (219) of anvil (218). Viewing angle (θ) may establish the relative visibility that a user has of distal most tip (219), such that the user can see in front of distal most tip (219) along any line of sight that passes through the intersection of sight line (240) and longitudinal axis (LA) within viewing angle (θ). As viewing angle (θ) increases, the user would have greater visibility of the area immediately in front of distal most tip (219) from proximal vantage points; whereas as viewing angle (θ) decreases, the user has less visibility of the area in front of distal most tip (219) from proximal vantage points. In some versions, viewing angle (θ) defines an angle greater than 90 degrees. Additionally, in some versions, viewing angle (θ) defines an angle greater than 135 degrees. In the illustrated version, the user generally looks along sight line (240) or along some other line of sight within viewing angle (θ), such that the user has visibility along sight line as well as any area within viewing angle (θ). The underside of distal most tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). In some instances, end effector (212) may be rotated before, during, or after clamping tissue (90). As a result, the tapered shape of anvil (218) may also provide more accessible viewing of distal most tip (219) or substantially adjacent distal most tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). Lower tapered surface (238) and the tapered shape of anvil (218) may provide a lead-in, guiding the rest of end effector (212) into the trocar. Visibility and maneuverability may thus be enhanced by the tapered design for both sides (241) of anvil (218) and each side (243) of cartridge (237).

In addition to the foregoing, end effector (212) and versions of instrument (10) incorporating end effector (212) may be configured and operable in accordance the teachings of any one or more of the patent references cited herein. Further modifications that may be incorporated into end effector (212) will be described in greater detail below.

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then be removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages, such as enhanced visualization, maneuverability, and/or tissue-gathering effects. However, in versions where all the structures of end effector (212) are rigid, the bent configuration of distal most tip (219) of anvil (218) may not lend itself well to marching operations, as distal most tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all the tissue that is to be cut and stapled is gathered proximal to distal most tip (219).

In view of the foregoing, it may be desirable to provide a variation of end effectors (12, 212) that provides the marching capabilities of end effector (12), the improved visibility, maneuverability, and tissue-gathering effects associated with end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. Providing a deformable tip can provide an additional level of maneuverability benefits in terms of navigating through tissue to a surgical site. In this manner, the deformable tip may deflect or deform to promote smooth and atraumatic movement of the end effector through tissue, particularly during marching operations.

III. SECOND EXEMPLARY SURGICAL INSTRUMENT INCLUDING END EFFECTOR WITH PLACEMENT TIP

FIGS. 11-24 show a second exemplary instrument (310) with exemplary end effectors (312, 412, 512) and exemplary placement tips (314, 414, 514). Instrument (310) may have a modular configuration such that shaft (322) is selectively removable from, and selectively attachable to, handle portion (320). Instrument (310) is configured similarly to instrument (10), such that the operability and use of instrument (310) is the same as described above for instrument (10) with the added feature of instrument (310) having a modular configuration. With its modular configuration, instrument (310) provides a way to change the desired end effector. Features operable for providing the modular configuration of instrument (310) may be configured in accordance with at least some of the teachings of U.S. Pub. No. 2017/0086823 entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

As will be discussed in greater detail below, end effectors (312, 412, 512) are provided on shaft (322) that is detachable from handle portion (320). End effectors (312, 412, 512) are operable to compress, staple, and cut tissue. End effectors (312, 412, 512) may be used in place of end effector (12) shown in FIG. 1. In some versions, end effectors (312, 412, 512) may be integrally formed with shaft (322) or, alternatively, may be separately formed and subsequently combined. In some versions, end effectors (312, 412, 512) may be provided for use in robotic systems. In such robotic systems, modular shaft (322) having any of the following end effectors (312, 412, 512) may be attachable to a portion of the robotic system for use such that handle portion (320) is replaced by components of the robotic system, including a body. Other ways to incorporate end effectors (312, 412, 512) having any of the following placement tips (314, 414, 514) into a user operated or robotic operated instrument will be apparent to those of ordinary skill in the art.

Figure 11:
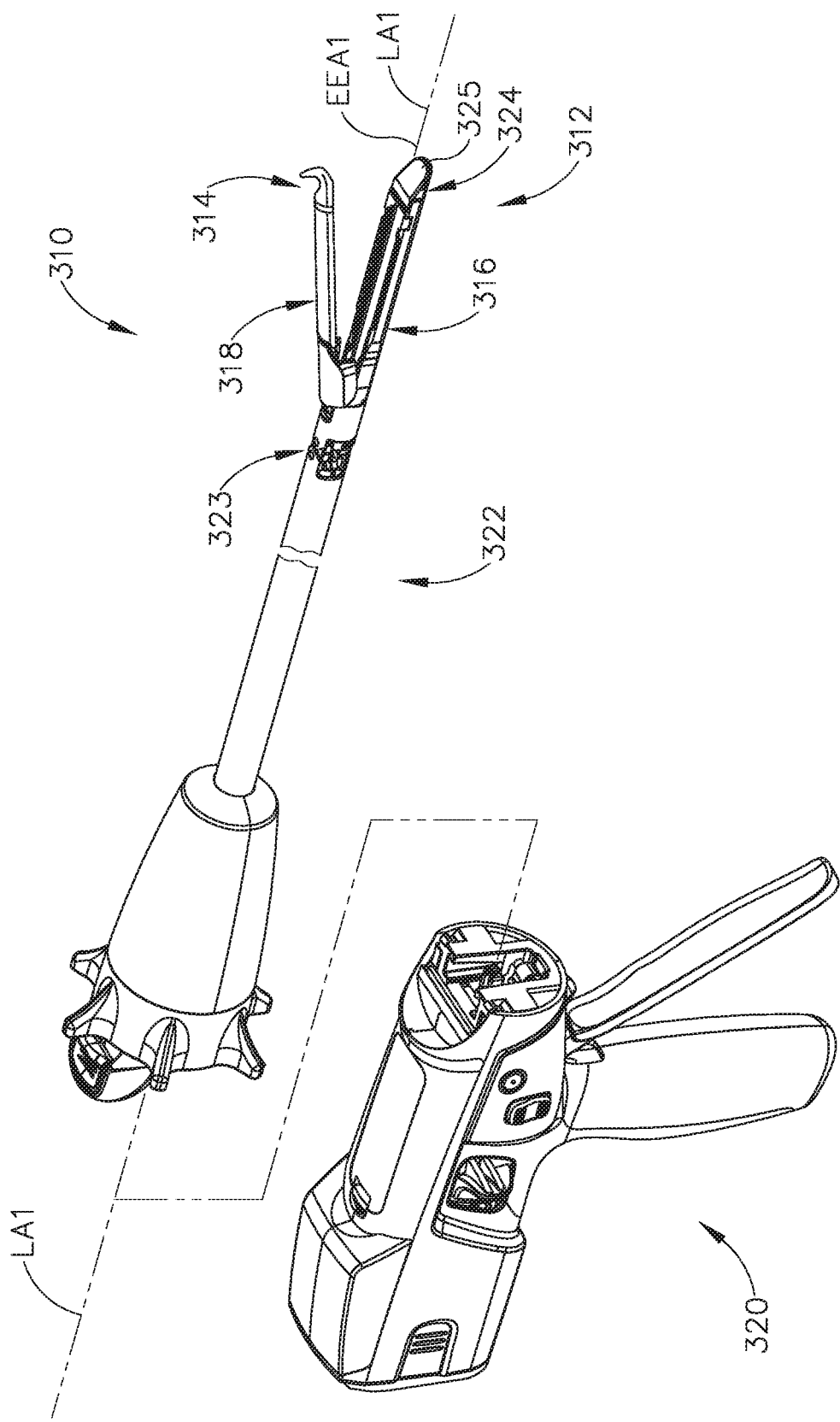
FIG. 11 depicts a perspective view of a second exemplary surgical stapling instrument with a third exemplary end effector with a first exemplary placement tip, where the upper and lower jaws are in an open configuration.

Placement tips (314, 414, 514) are operable to elastically deform from a non-deflected position to a deflected position. Placement tips (314, 414, 514) obtain the non-deflected position when end effectors (312, 412, 512) are not clamping tissue. More specifically, in this non-deflected position, end effectors (312, 412, 512) may be in the open configuration as shown in FIG. 11, or in the closed configuration as shown in FIGS. 8 and 9 with respect to end effector (212). In instances when end effectors (312, 412, 512) are in this non-deflected position, end effectors (312, 412, 512) may be considered in a non-loaded state or non-loaded position. Conversely, in the deflected position (not shown) when end effectors (312, 412, 512) are clamping tissue, end effectors (312, 412, 512) may be considered in a loaded state or a loaded position. In the deflected position, at least a portion of placement tips (314, 414, 514) deflect upwardly. The deflected position for placement tips (314, 414, 514) may be substantially straight in some versions, but may be deflected to a degree (e.g., slightly above or slightly below end effector axis (EEA1, EEA2, EEA3)) in other versions. It should be understood that the deflected position for placement tips (314, 414, 514) may be defined by the characteristics (e.g., thickness, density, etc.) of the tissue that is being captured between respective lower jaws (316, 416, 516) and anvils (318, 418, 518), thereby causing the deflection of placement tips (314, 414, 514). In some variations, placement tips (314, 414, 514) do not deflect in response to a load.

The placement tips (314, 414, 514) described below may be used with any surgical instrument (10, 310) described above and below and in any of the various procedures described in the various patent references cited herein. As will be described in greater detailed below, placement tips (314, 414, 514) may be used singularly or in combination with other placement tips, such as placement tips (314, 414, 514). To this end, like numbers below indicate like features described above. Except as otherwise described below, instrument (310) described below may be constructed and operable like instrument (10) described above. Certain details of instrument (310) will therefore be omitted from the following description, it being understood that such details are already provided above in the description of instrument (10). Other suitable ways in which various surgical instruments may be used will be apparent to those of ordinary skill in the art in view of the teachings herein.

It should also be understood that the teachings herein may be readily combined with various teachings in U.S. Patent Pub. No. 2020/0015813, entitled "Surgical Stapling End Effector Component with Articulation and Asymmetric Deformable Tip," published Jan. 16, 2020, the disclosure of which is incorporated by reference herein. Various suitable ways in which the teachings herein may be combined with the teachings of U.S. Patent Pub. No. 2020/0015813 will be apparent to those of ordinary skill in the art.

A. Second Exemplary Surgical Instrument Including Third End Effector with First Example of Placement Tip FIGS. 11-14 show surgical instrument (310), configured as a surgical stapler, that comprises a third exemplary end effector (312) and a first exemplary placement tip (314). End effector (312) includes an upper jaw and a lower jaw (316), with the upper jaw including an anvil (318). Instrument (310) additionally includes a body, shown as a handle portion (320), and a shaft (322) that extends from handle portion (320). As shown in FIG. 11, shaft (322) defines a longitudinal axis (LA1) that is colinear with an end effector axis (EEA1) of end effector (312), but which may noncolinear, and instead angled, when end effector (312) is articulated relative to shaft (322) using articulation joint (323).

Figure 12:
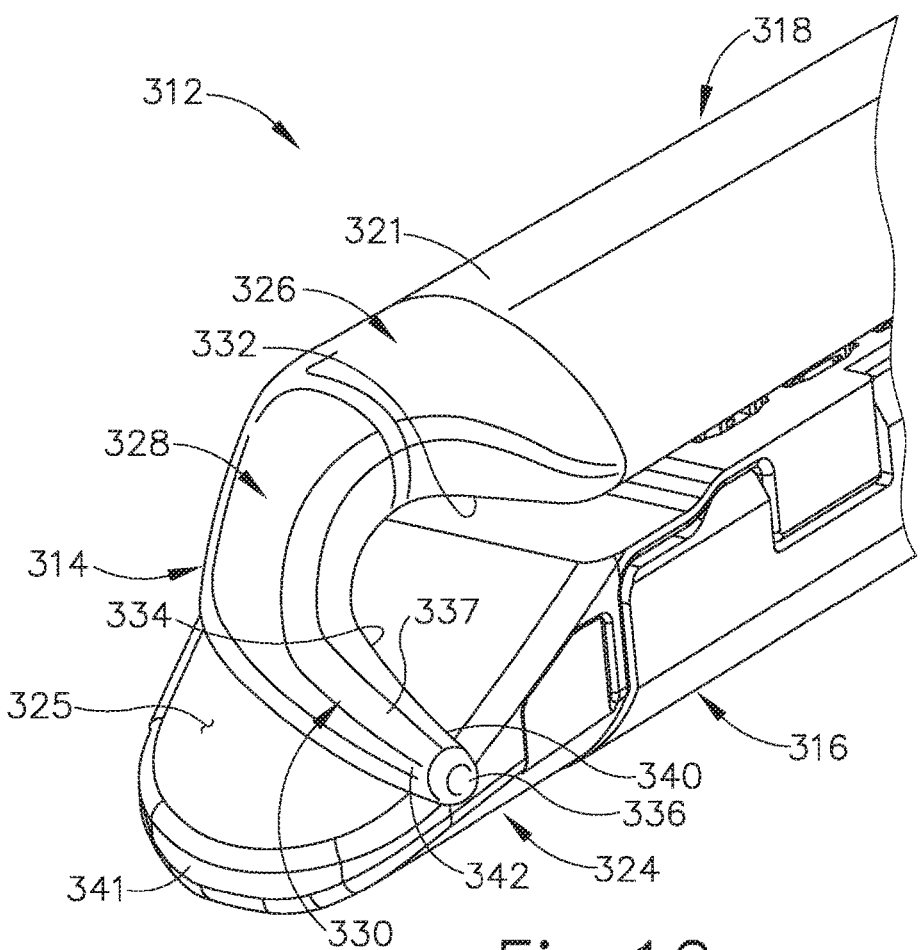
FIG. 12 depicts an enlarged perspective view of a distal portion of the end effector of FIG. 11, with the upper and lower jaws in a closed configuration.
Figure 13:
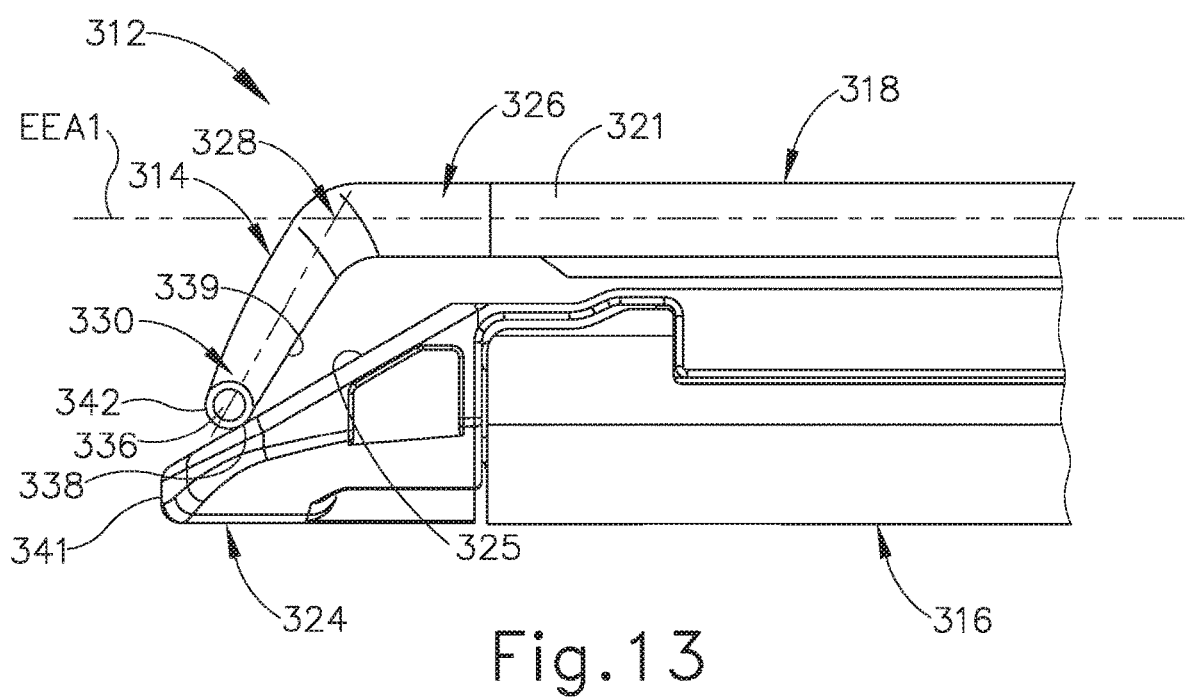
FIG. 13 depicts a side view of the distal portion of the end effector of FIG. 11 in the closed configuration.
Figure 14:
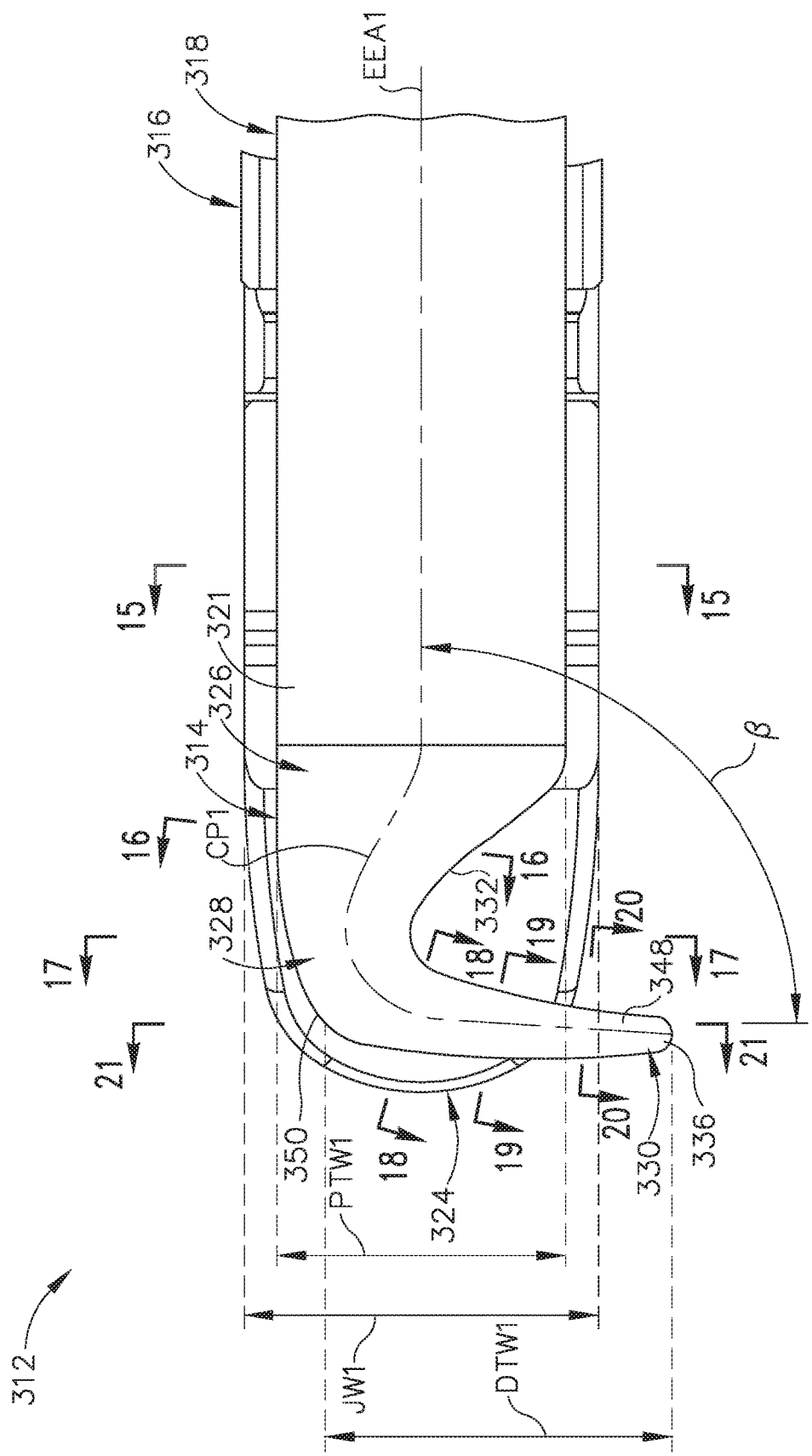
FIG. 14 depicts a top view of the end distal portion of the effector of FIG. 11.

FIGS. 12-14 show enlarged views of a distal end of end effector (312). Placement tip (314) is located adjacent at least one of a distal end (321) of anvil (318) or a distal end of lower jaw (316). As shown in FIGS. 11-14, placement tip (314) is coupled with distal end (321) of anvil (318). Placement tip (314) may be permanently coupled with anvil (318), or alternatively, placement tip (314) may be removably coupled with anvil (318). Placement tip (314) may be integrally formed together with anvil (318) as unitary piece or consist of separately formed components. Placement tip (314) may be positioned on the same jaw as staple cartridge (324) or on the same jaw as anvil (318). As shown in FIG. 11, upper jaw includes anvil (318), while lower jaw (316) is removably coupled with staple cartridge (324). However, this relationship may be reversed if desired. Staple cartridge (324) is configured to hold one or more staples in a manner similar to staple cartridge (37). As previously described, at least one of anvil (318) or lower jaw (316) is movable relative to other of anvil (318) or lower jaw (316) between the open configuration and the closed configuration. As shown, anvil (318) pivotably rotates toward lower jaw (316) in the same manner as anvil (18) as described above with respect to instrument (10). In this manner, end effector (312) is like end effector (12), except for the laterally deflected configuration and deformability of placement tip (314).

FIGS. 12-13 show placement tip (314) as including a proximal portion (326), a central portion (328), and a distal portion (330). Proximal portion (326) extends distally from distal end (321) of anvil (318) and is disposed opposite from lower jaw (316). Central portion (328) is disposed longitudinally between proximal and distal portions (326, 330). Central portion (328) and distal portion (330) of placement tip (314) each include an asymmetric profile along longitudinal axis of end effector (312), i.e. end effector axis (EEA1). FIGS. 12 and 14 show central portion (328) tapering inwardly along an inwardly tapering portion (332) on the left side (when viewed from above), then tapering outwardly along an outwardly tapering portion (334). The radius of curvature of the inwardly and outwardly tapering portions (332, 334) may be constant or changing. Additionally, as shown in FIG. 12, the opposite right side (when viewed from above) extends arcuately toward distal portion (330). As shown, placement tip (314) terminates at a tip end (336). Placement tip (314) is thus generally C-shaped in this example. As shown in FIG. 13, in the closed configuration, a contacting portion (338) of distal portion (330) is in abutting contact with a distal angled surface (325) of staple cartridge (324). Alternatively, a gap may exist between placement tip (314) and distal angled surface (325) of staple cartridge (324). Also, an underside surface (339) of placement tip (314) is disposed at an angle relative to distal angled surface (325) of staple cartridge (324). In other words, underside surface (339) is not parallel to distal angled surface (325); but may be parallel if desired.

Figure 15:
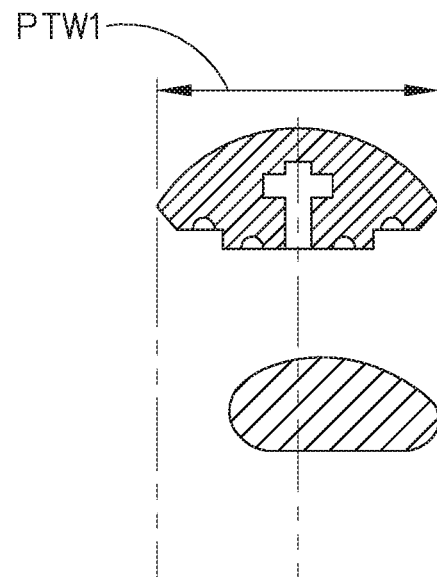
FIG. 15 depicts a cross-sectional view of the anvil of the end effector of FIG. 11, taken along line 15-15 of FIG. 14.
Figure 16:
FIG. 16 depicts a cross-sectional view of the placement tip of the end effector of FIG. 11, taken along line 16-16 of FIG. 14.
Figure 17:
FIG. 17 depicts a cross-sectional view of the placement tip of the end effector of FIG. 11, taken along line 17-17 of FIG. 14.
Figure 18:
FIG. 18 depicts a cross-sectional view of the placement tip of the end effector of FIG. 11, taken along line 18-18 of FIG. 14.
Figure 19:
FIG. 19 depicts a cross-sectional view of the placement tip of the end effector of FIG. 11, taken along line 19-19 of FIG. 14.
Figure 20:
FIG. 20 depicts a cross-sectional view of the placement tip of the end effector of FIG. 11, taken along line 20-20 of FIG. 14.

Placement tip (314) generally follows a curvilinear path (CP1) along proximal, central, and distal portions (326, 328, 330) toward tip end (336). FIG. 14 and the cross-sections of FIGS. 15-20 show successive perimeters of anvil (318) or placement tip (314) taken perpendicular to curvilinear path (CP1). More specifically, FIG. 15 shows a cross-section of anvil (318), while FIGS. 16-20 show cross-sections of placement tip (314) taken at various locations along proximal, central, and distal portions (326, 328, 330). The perimeters of the successive cross-sections of FIGS. 15-20 decrease moving along curvilinear path (CP1) toward tip end (336). For example, the perimeter of the cross-section shown in FIG. 15 is greater than the perimeter of the cross-section shown in FIG. 16, which is greater than perimeter of the cross-section shown in FIG. 17, which is greater than the perimeter of the cross-section shown in FIG. 18. Likewise, the perimeter of the cross-section shown in FIG. 18 is greater than the perimeter of the cross-section shown in FIG. 19, which is greater than the perimeter of the cross-section shown in FIG. 20.

Regarding the lateral widths shown in FIG. 14, distal portion (330) of placement tip (314) has a lateral width that is greater than the lateral width of the opposing jaw, shown as lower jaw (316). As used herein, the lateral width is measured perpendicular to end effector axis (EEA1). More specifically, as shown in FIG. 14, proximal portion (326) has a proximal tip width (PTW1) that is less than a jaw width (JW1) of lower jaw (316) disposed opposite placement tip (314). For example, proximal tip width (PTW1) may be measured where placement tip (314) couples with distal end (321) of anvil (318). As shown in FIGS. 14-15, proximal tip width (PTW1) has the same lateral width as anvil (318). Central portion (328) has a lateral width that is less than the lateral width of proximal portion (326).

Figure 21:
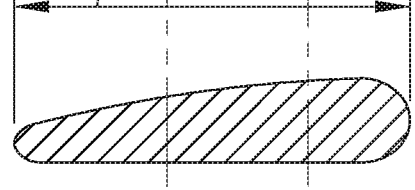
FIG. 21 depicts a cross-sectional view of the placement tip of the end effector of FIG. 11, taken along line 21-21 of FIG. 14.

Distal portion (330) has a distal tip width (DTW1) depicted in the cross-section of FIG. 21 that is greater than jaw width (JW1) of lower jaw (316) disposed opposite placement tip (314). Unlike the cross-sections of FIG. 16 and FIGS. 18-20 that are taken perpendicular to curvilinear path (CP1) but are not perpendicular to end effector axis (EEA1), FIG. 21 is taken perpendicular to end effector axis (EEA1), similar to FIGS. 15 and 17. As shown in FIG. 14, distal portion (330) includes an overhang portion (348) that extends beyond the opposite jaw only on a single lateral side. However, an angled portion (350) may extend laterally beyond the width of lower jaw (316) or the width of staple cartridge (324), such that placement tip (314) extends beyond both lateral sides (i.e. left and right sides) of lower jaw (316) or staple cartridge (324). Tip end (336) includes a proximal surface (340) and a distal surface (342), with proximal surface (340) extending adjacent outwardly tapering portion (334). Additionally, as shown in FIGS. 13 and 14, a distal tip (341) of staple cartridge (324) extends distally beyond distal surface (342) of tip end (336). In other words, lower jaw (316) extends distally beyond tip end (336) of placement tip (314). However, lower jaw (316) may be shorter and/or and narrower than anvil (318) and placement tip (314) if desired.

Distal portion (330) includes a tip axis (TA1) defined by the direction that tip end (336) of distal portion (330) extends. In the example shown, tip axis (TA1) is measured using proximal surface (340) of placement tip (314). Alternatively, other surfaces (e.g. distal surface (342)) may also be used. As shown in FIG. 14, tip axis (TA1) is generally perpendicular to end effector axis (EEA1) and longitudinal axis (LA1) of shaft (322). In other words, the angle beta (β) formed between tip end (336) and end effector axis (EEA1) is about 90 degrees. However, this non-zero angle may vary. As shown in FIGS. 12 and 14, given the geometry of placement tip (314), distal portion (330) of placement tip (314) is configured to deflect proximally as placement tip (314) is advanced distally through the trocar of a patient.

Figure 22:
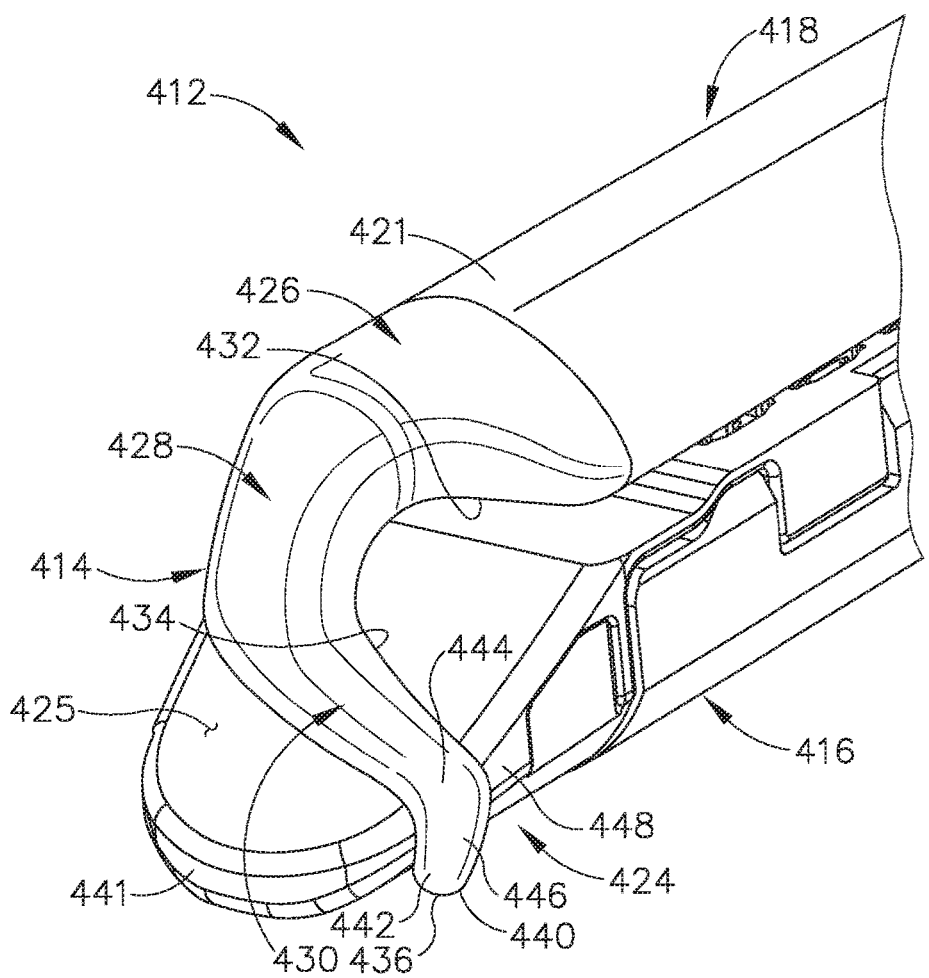
FIG. 22 depicts a perspective view of a distal portion of a fourth exemplary end effector with a second exemplary placement tip in a closed configuration.
Figure 23:
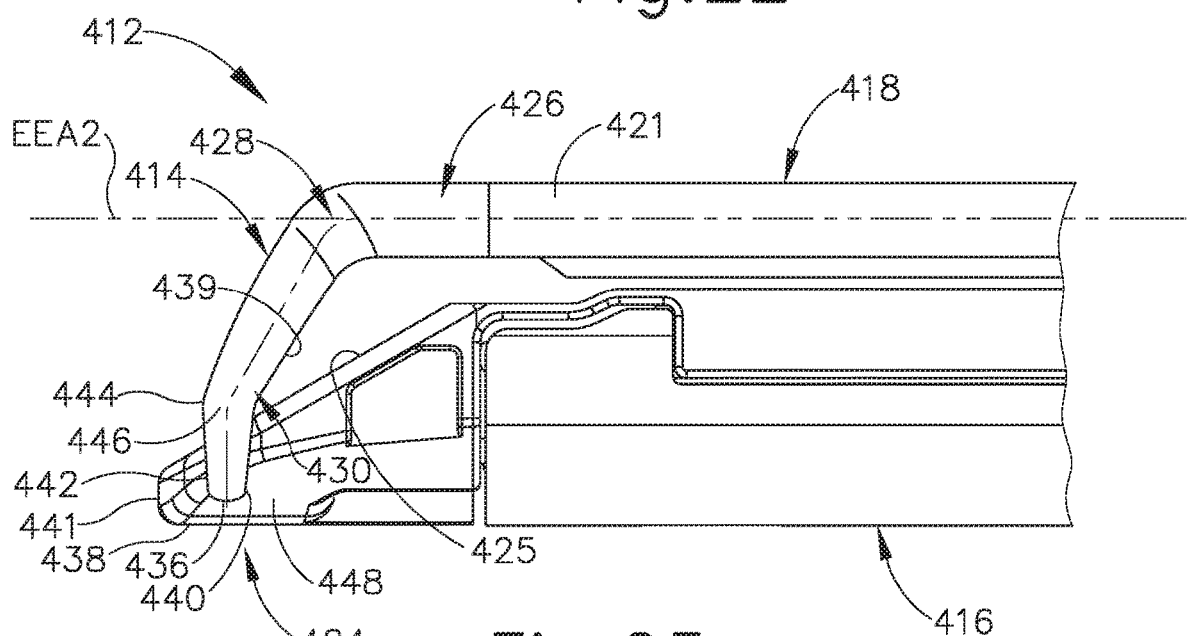
FIG. 23 depicts a side view of the distal portion of the end effector of FIG. 22.
Figure 24:
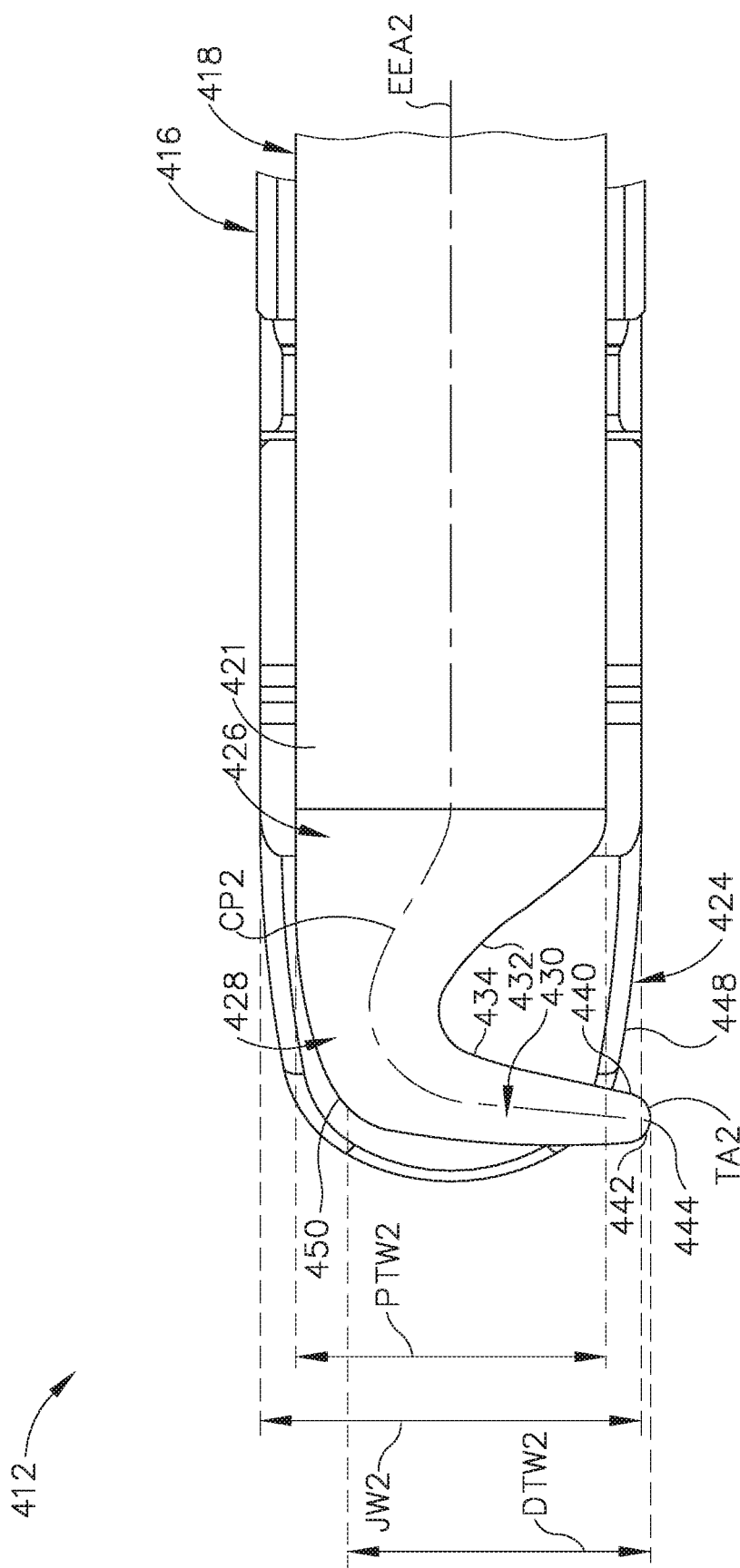
FIG. 24 depicts a top view of the distal portion of the end effector of FIG. 22 in the closed configuration.

B. Second Exemplary Surgical Instrument Including Fourth End Effector with Second Example of Placement Tip FIGS. 22-24 show a fourth exemplary end effector (412) and a second exemplary placement tip (414). End effector (412) and placement tip (414) are similar to end effector (312) and placement tip (314) described in connection to FIGS. 11-21 with notable differences indicated below. End effector (412) includes placement tip (414), a lower jaw (416), an anvil (418), a distal end (421), a staple cartridge (424), a distal angled surface (425), a proximal portion (426), a central portion (428), a distal portion (430), an inwardly tapering portion (432), an outwardly tapering portion (434), a tip end (436), an underside surface (439), a proximal surface (440), a distal surface (442), and an angled portion (450).

As shown in FIG. 22, the upper jaw includes anvil (418), and lower jaw (416) is like lower jaw (16, 316). Staple cartridge (424) is removably coupled with lower jaw (416) in a similar manner and function as lower jaws (16, 316) and staple cartridges (37, 324) described above. At least one of lower jaw (416) or anvil (418) is movable relative to the other of lower jaw (416) or anvil (418) between an open configuration (shown in FIG. 11 with respect to end effector (312)) and a closed configuration (shown in FIGS. 22-23). Anvil (418) pivotably rotates toward lower jaw (416) in a similar manner to anvils (18, 318) as described above with respect to instruments (10, 310). End effector (412) is thus like effector (12), but with anvil (418) comprising placement tip (414) that is elastically deformable. While not shown, placement tip (414) may be located adjacent one or both of distal end (421) of anvil (418) or a distal end of lower jaw (416).

FIGS. 22-24 show placement tip (414) as including proximal, central, and distal portions (426, 428, 430). Proximal portion (426) extends distally from distal end (421) of anvil (418) and is disposed opposite from lower jaw (416). Central portion (428) is disposed longitudinally between proximal and distal portions (426, 430). Central portion (428) and distal portion (430) of placement tip (414) each include an asymmetric profile along an end effector axis (EEA2). As shown in FIGS. 22 and 24, central portion (428) tapers inwardly along inwardly tapering portion (432), then tapers outwardly along outwardly tapering portion (434). The radius of curvature of inwardly and outwardly tapering portions (432, 434) may be constant or changing. Additionally, as shown in FIG. 24, the opposite side extends arcuately toward distal portion (430). Placement tip (414) terminates at tip end (436). Similar to placement tip (314) described relative to FIGS. 14-20, successive perimeters of placement tip (414) taken perpendicular to curvilinear path (CP2) decrease moving toward tip end (436).

As shown in FIG. 22, distal portion (430) extends downwardly at an overhang portion (444) toward lower jaw (416) and staple cartridge (424), in a manner that differs from placement tip (314). Moreover, as shown in FIG. 23, a projection (446) of distal portion (430) extends below distal angled surface (425) of staple cartridge (424) and approaches a bottom surface (438) of staple cartridge (424). As shown, tip end (436) extends parallel to and is separated a distance from a tapered side surface (448) of staple cartridge (424) in the closed configuration. Alternatively, tip end (436) may extend parallel to and be in contact with tapered side surface (448) of staple cartridge (424) in the closed configuration.

Regarding the lateral widths shown in FIG. 24, distal portion (430) of placement tip (414) has a lateral width that is less than the lateral width of the opposing jaw, shown as lower jaw (416). As used herein, the lateral width is measured perpendicular to end effector axis (EEA2). More specifically, as shown in FIG. 24, proximal portion (426) has a proximal tip width (PTW2) that is less than a jaw width (JW2) of lower jaw (416) disposed opposite placement tip (414). Proximal tip width may be measured where placement tip (414) couples with distal end (421) of anvil (418). Additionally, distal portion (430) has a distal tip width (DTW2) that is less than jaw width (JW2) of lower jaw (416) disposed opposite placement tip (414).

Additionally, distal portion (430) includes overhang portion (444) that extends beyond the opposite jaw only on one lateral side. However, an angled portion (435) may extend laterally beyond the width of lower jaw (416) or the width of staple cartridge (424), such that placement tip (414) extends beyond both lateral sides of lower jaw (416) or staple cartridge (424). Central portion (428) has a lateral width that is less than the lateral width of proximal portion (426). Additionally, lower jaw (416) extends distally beyond tip end (436) of placement tip (414). More specifically, as shown in FIG. 23, a distal tip (441) of staple cartridge (424) extends distally beyond distal surface (442) of tip end (436). However, lower jaw (416) may be shorter and/or and narrower than anvil (418) and placement tip (414) if desired.

Figure 25:
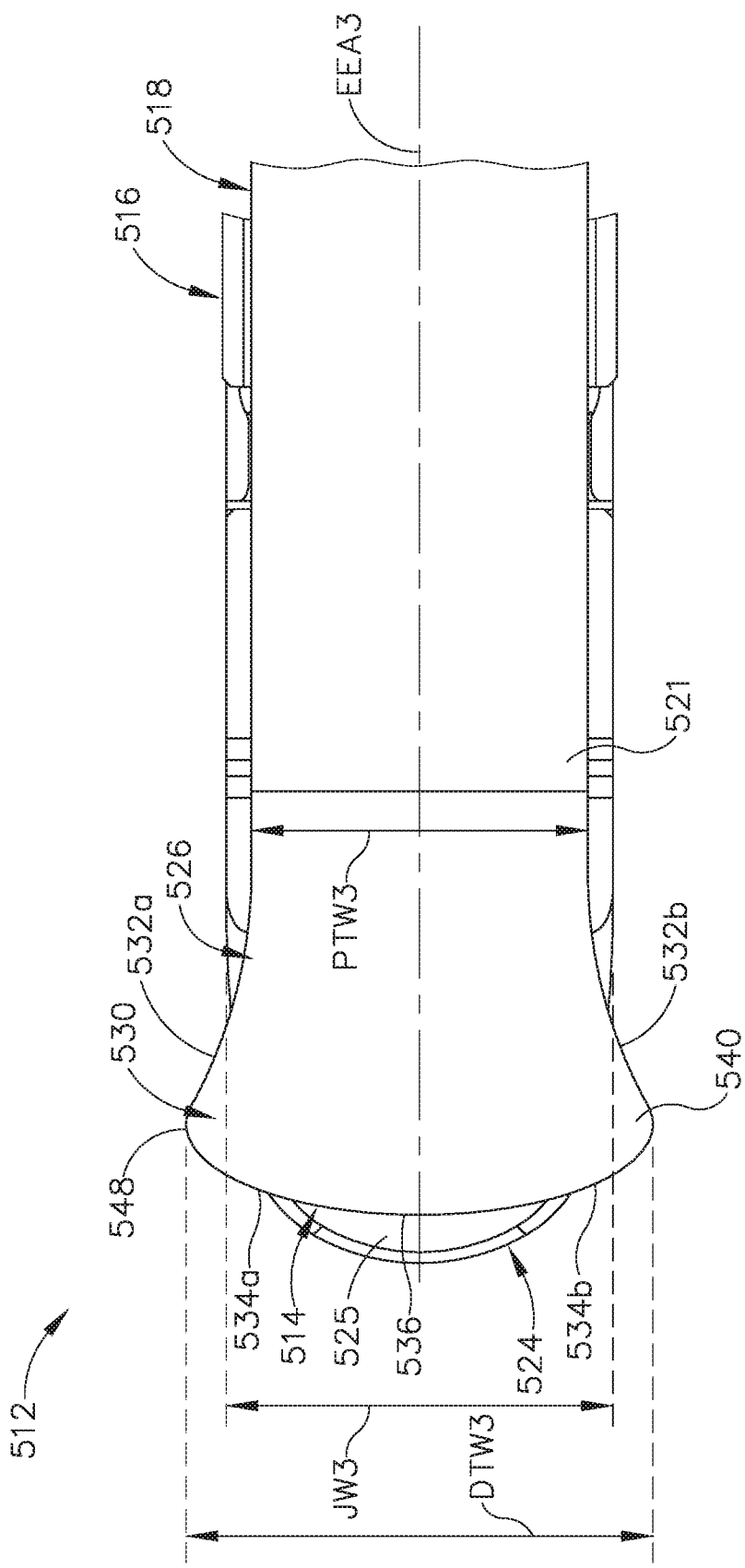
FIG. 25 depicts a perspective view of a distal portion of a fifth exemplary end effector with a third exemplary placement tip in a closed configuration.

C. Second Exemplary Surgical Instrument Including Fifth End Effector with Third Example of Placement Tip FIG. 25 shows a fifth exemplary end effector (512) and a third exemplary placement tip (514). End effector (512) and placement tip (514) are similar to end effector (312) and placement tip (314) described in connection to FIGS. 11-21 with notable differences indicated below. End effector (512) includes placement tip (514), a lower jaw (516), an anvil (518), a distal end (521), a staple cartridge (524), a distal angled surface (525), a proximal portion (526), and a distal portion (530).

As shown in FIG. 25, the upper jaw includes anvil (518), and lower jaw (516) is like lower jaws (16, 316). Staple cartridge (524) is removably coupled with lower jaw (516) in a similar manner and function as lower jaws (16, 316) and staple cartridges (37, 324) described above. At least one of lower jaw (516) or anvil (518) is movable relative to the other of lower jaw (516) or anvil (518) between an open configuration (shown in FIG. 11 with respect to end effector (312)) and a closed configuration (shown generally in FIG. 25). Anvil (518) pivotably rotates toward lower jaw (516) in a similar manner to anvils (18, 318) as described above with respect to instruments (10, 310). End effector (512) is thus like effector (12), but with anvil (518) comprising placement tip (514) that is elastically deformable. While not shown, placement tip (514) may be located adjacent one or both of distal end (521) of anvil (518) or a distal end of lower jaw (516).

FIG. 25 shows placement tip (514) as including proximal and distal portions (526, 530) that are each symmetric along an end effector axis (EEA3). Proximal portion (526) extends distally from distal end (521) of anvil (518) and is disposed opposite from lower jaw (516). Distal portion (530) tapers outwardly along outwardly tapering portions (532a-b), then tapers inwardly along inwardly tapering portions (534a-b). The radius of curvature of inwardly and outwardly tapering portions (532a-b, 534a-b) may be constant or changing. Placement tip (514) terminates at a tip end that is along end effector axis (EEA3).

Regarding the lateral widths shown in FIG. 25, distal portion (530) of placement tip (514) has a lateral width that is greater than the lateral width of the opposing jaw, shown as lower jaw (516). As used herein, the lateral width is measured perpendicular to end effector axis (EEA3). More specifically, proximal portion (526) has a proximal tip width (PTW3) that is less than a jaw width (JW3) of lower jaw (516) disposed opposite placement tip (514). Proximal tip width (PTW3) may be measured where placement tip (514) couples with distal end (521) of anvil (518) is shown as the same as an anvil tip width.

Additionally, distal portion (530) has a distal tip width (DTW3) depicted in the cross-section of FIG. 25 that is greater than jaw width (JW3) of lower jaw (516) disposed opposite placement tip (514). Additionally, distal portion (530) includes first and second overhang portions (538, 540) that each extend beyond the lateral width of the opposite jaw on both lateral sides. As shown, placement tip (514) extends beyond both lateral sides (left and right sides) of both lower jaw (516) and staple cartridge (524). First and second overhang portions (538, 540) are symmetric about end effector axis (EEA3). As shown, lower jaw (516) extends distally beyond tip end (536) of placement tip (514). However, lower jaw (516) may be shorter and/or and narrower than anvil (518) and placement tip (514) if desired.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An instrument, comprising: (a) a body; (b) a shaft extending from the body; and (c) an end effector in communication with the shaft, wherein the end effector defines a longitudinal axis, wherein the end effector is operable to compress, staple, and cut tissue, wherein the end effector comprises: (i) first and second opposing jaws, wherein at least one of the first and second jaws is movable relative to the other of the first and second jaws between an open configuration and a closed configuration, (ii) a staple cartridge configured to hold one or more staples, wherein the staple cartridge is coupled with the second jaw, and (iii) a placement tip extending from a distal end of the first jaw or a distal end of the second jaw, wherein the placement tip extends along a curvilinear path and terminates at a tip end, wherein the placement tip is configured such that successive perimeters of the placement tip taken perpendicular to the curvilinear path decrease moving toward the tip end, and wherein the tip end extends at a non-zero angle relative to the longitudinal axis of the end effector.

Example 2

The instrument of Example 1, wherein the first jaw includes an anvil coupled with the placement tip, and wherein the second jaw is removably coupled with the staple cartridge.

Example 3

The instrument of any one or more of Examples 1 through 2, wherein the placement tip extends from the distal end of the first jaw, and wherein the placement tip is configured to contact the staple cartridge in the closed position.

Example 4

The instrument of any one or more of Examples 1 through 3, wherein the second jaw is configured to extend distally beyond the tip end of the placement tip.

Example 5

The instrument of any one or more of Examples 1 through 4, wherein the placement tip includes a distal portion that is configured to contact a distal angled surface of the staple cartridge in the closed position.

Example 6

The instrument of any one or more of Examples 1 through 5, wherein the tip end is configured to extend parallel to and contact a lateral side of the staple cartridge in the closed position.

Example 7

The instrument of any one or more of Examples 1 through 6, wherein the tip end is configured to extend parallel to and be separated a distance from a lateral side of the staple cartridge in the closed position.

Example 8

The instrument of any one or more of Examples 1 through 7, wherein a distal portion of the placement tip has an asymmetric profile along the longitudinal axis of the end effector.

Example 9

The instrument of any one or more of Examples 1 through 8, wherein a distal portion of the placement tip is configured to deflect proximally as the placement tip is advanced distally through a trocar of a patient.

Example 10

The instrument of any one or more of Examples 1 through 9, wherein the distal portion includes a first overhang portion that extends beyond the opposite jaw only on one lateral side of the staple cartridge.

Example 11

The instrument of any one or more of Examples 1 through 10, wherein the angle formed between the of the tip end and the longitudinal axis is about 90 degrees.

Example 12

The instrument of any one or more of Examples 1 through 11, wherein the placement tip is C-shaped.

Example 13

The instrument of any one or more of Examples 1 through 12, wherein the placement tip includes proximal and distal portions, wherein the proximal portion has a proximal tip width that is less than a jaw width of the jaw disposed opposite the placement tip, and wherein the distal portion has a distal tip width that is greater than the jaw width of the jaw disposed opposite the placement tip.

Example 14

The instrument of any one or more of Examples 1 through 13, wherein the placement tip includes proximal and distal portions, wherein the distal portion has a lateral width that is greater than a lateral width of the opposing jaw.

Example 15

The instrument of any one or more of Examples 1 through 14, wherein the placement tip includes a central portion disposed between the proximal and distal portions, wherein the central portion has a lateral width that is less than a lateral width of the proximal portion, and wherein the lateral width of the proximal portion is less than a lateral width of the opposing jaw.

Example 16

An instrument, comprising: (a) a body; (b) a shaft extending from the body; and (c) an end effector in communication with the shaft, wherein the end effector defines a longitudinal axis, wherein the end effector is operable to compress, staple, and cut tissue, wherein the end effector comprises: (i) first and second opposing jaws, wherein at least one of the first and second jaws is movable relative to the other of the first and second jaws between an open position and a closed position, (ii) a staple cartridge configured to hold one or more staples, wherein the staple cartridge is coupled with the second jaw, and (iii) a placement tip extending from a distal end of the first jaw or a distal end of the second jaw, wherein the placement tip comprises: (A) a proximal portion having a proximal tip width, and (B) a distal portion having a distal tip width that is greater than a jaw width of the jaw disposed opposite the placement tip.

Example 17

The instrument of any one or more of Examples 1 through 16, wherein the distal portion includes a first overhang portion that extends beyond the opposite jaw only on one lateral side of the staple cartridge.

Example 18

The instrument of any one or more of Examples 1 through 17, wherein the distal portion includes first and second overhang portions that extend beyond the width of the opposite jaw on both lateral sides, wherein the first and second overhang portions are symmetric about the longitudinal axis of the end effector.

Example 19

The instrument of any one or more of Examples 1 through 18, wherein the instrument comprises an end effector including first and second oppositely disposed jaws, the placement tip comprising: (a) a proximal portion having a proximal tip width; and (b) a distal portion having a distal tip width that is greater than a jaw width of the jaw disposed opposite the placement tip.

Example 20

The instrument of any one or more of Examples 1 through 19, wherein the distal portion includes first and second overhang portions that extend beyond the width of the opposite jaw on both lateral sides, wherein the first and second overhang portions are symmetric about the longitudinal axis of the end effector.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. Patent Pub. No. 2018/0325516, entitled "Method of Surgical Stapling with End Effector Component Having a Curved Tip," published Nov. 15, 2018, the disclosure of which is incorporated by reference herein. Various suitable ways in which the teachings herein may be combined with the teachings of U.S. Patent Pub. No. 2018/0325516 will be apparent to those of ordinary skill in the art.

It should also be understood that the teachings herein may be readily combined with various teachings in U.S. Patent Pub. No. 2018/0325515, entitled "Surgical Stapling End Effector Jaw with Tip Deflecting Toward Other Jaw," published Nov. 15, 2018, issued as U.S. Pat. No. 11,103,244 on Aug. 31, 2021, the disclosure of which is incorporated by reference herein. Various suitable ways in which the teachings herein may be combined with the teachings of U.S. Patent Pub. No. 2018/0325515 , issued as U.S. Pat. No. 11,103,244 on Aug. 31, 2021, will be apparent to those of ordinary skill in the art.

It should also be understood that the teachings herein may be readily combined with various teachings in U.S. Patent Pub. No. 2018/0325514, entitled "Surgical Stapling End Effector Component with Tip Having Varying Bend Angle," published Nov. 15, 2018, the disclosure of which is incorporated by reference herein. Various suitable ways in which the teachings herein may be combined with the teachings of U.S. Patent Pub. No. 2018/0325514 will be apparent to those of ordinary skill in the art.

It should also be understood that the teachings herein may be readily combined with various teachings in U.S. Patent Pub. No. 2020/0015815, entitled "Permanent Attachment Means for Curved Tip of Component of Surgical Stapling Instrument," published Jan. 16, 2020, issued as U.S. Pat. No.

10,973,515 on Apr. 13, 2021, the disclosure of which is incorporated by reference herein. Various suitable ways in which the teachings herein may be combined with the teachings of U.S. Patent Pub. No. 2020/0015815, issued as U.S. Pat. No. 10,973,515 on Apr. 13, 2021, will be apparent to those of ordinary skill in the art.

It should also be understood that the teachings herein may be readily combined with various teachings in U.S. Patent Pub. No. 2020/0015811, entitled "Surgical Stapling End Effector Component with Deformable Tip Having Void," published Jan. 16, 2020, the disclosure of which is incorporated by reference herein. Various suitable ways in which the teachings herein may be combined with the teachings of U.S. Patent Pub. No. 2020/0015811 will be apparent to those of ordinary skill in the art.

It should also be understood that the teachings herein may be readily combined with various teachings in U.S. Patent Pub. No. 2020/0015814, entitled "Surgical Stapling End Effector Component with Deformable Tip Having Thick Distal End," published Jan. 16, 2020, the disclosure of which is incorporated by reference herein. Various suitable ways in which the teachings herein may be combined with the teachings of U.S. Patent Pub. No. 2020/0015814 will be apparent to those of ordinary skill in the art.

It should also be understood that the teachings herein may be readily combined with various teachings in U.S. Patent Pub. No. 2020/0015817, entitled "Buttress Applier Cartridge for Surgical Stapler Having End Effector with Deflectable Curved Tip," published Jan. 16, 2020, issued as U.S. Pat. No. 10,786,252 on Sep. 29, 2020, the disclosure of which is incorporated by reference herein. Various suitable ways in which the teachings herein may be combined with the teachings of U.S. Patent Pub. No. 2020/0015817, issued as U.S. Pat. No. 10,786,252 on Sep. 29, 2020 will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument, comprising:
    (a) a body;
    (b) a shaft extending from the body; and
    (c) an end effector in communication with the shaft, wherein the end effector defines a longitudinal axis, wherein the end effector is operable to compress, staple, and cut tissue, wherein the end effector comprises:
        (i) first and second opposing jaws, wherein at least one of the first and second jaws is movable relative to the other of the first and second jaws between an open configuration and a closed configuration,
        (ii) a staple assembly configured to hold one or more staples, wherein the staple assembly is coupled with the second jaw, wherein the staple assembly includes first and second lateral sides disposed opposite one another and generally parallel to the longitudinal axis, and
        (iii) a placement tip extending from a distal end of the first jaw or a distal end of the second jaw, wherein the placement tip includes a curved portion that extends along a curvilinear path, wherein the curved portion extends laterally beyond one of the first or second lateral sides and away from the first and second lateral sides, wherein the placement tip tapers along the entirety of the curved portion.

2. The instrument of claim 1, wherein the staple assembly includes a staple cartridge, wherein the first jaw includes an anvil coupled with the placement tip, and wherein the second jaw is removably coupled with the staple cartridge.

3. The instrument of claim 1, wherein the placement tip extends from the distal end of the first jaw, and wherein the placement tip is configured to contact the staple assembly in the closed position.

4. The instrument of claim 1, wherein the second jaw is configured to extend distally beyond the tip end of the placement tip.

5. The instrument of claim 1, wherein the placement tip includes a distal portion that is configured to contact a distal angled surface of the staple assembly in the closed position.

6. The instrument of claim 1, wherein a distal portion of the placement tip has an asymmetric profile along the longitudinal axis of the end effector.

7. The instrument of claim 1, wherein a distal portion of the placement tip is configured to deflect proximally as the placement tip is advanced distally through a trocar of a patient.

8. The instrument of claim 1, wherein a distal portion of the placement tip includes a first overhang portion that extends laterally beyond the opposite jaw only on one of the first or second lateral sides of the staple assembly.

9. The instrument of claim 1, wherein the angle formed between the tip end and the longitudinal axis is about 90 degrees.

10. The instrument of claim 1, wherein the placement tip is C-shaped.

11. The instrument of claim 1, wherein the placement tip includes proximal and distal portions, wherein the proximal portion has a proximal tip width that is less than a jaw width of the jaw disposed opposite the placement tip, and wherein the distal portion has a distal tip width that is greater than the jaw width of the jaw disposed opposite the placement tip.

12. The instrument of claim 1, wherein the placement tip includes proximal and distal portions, wherein the distal portion has a lateral width that is greater than a lateral width of the opposing jaw.

13. The instrument of claim 12, wherein the placement tip includes a central portion disposed between the proximal and distal portions, wherein the central portion has a lateral width that is less than a lateral width of the proximal portion, and wherein the lateral width of the proximal portion is less than a lateral width of the opposing jaw.

14. The instrument of claim 1, wherein the staple assembly includes a distal surface disposed between the first and second lateral sides, wherein the curvilinear path curves away from the longitudinal axis and toward one of the first or second lateral sides and also towards the distal contact surface.

15. The instrument of claim 1, wherein successive perimeters of the placement tip taken perpendicular to the curvilinear path continually decrease moving toward the tip end.

16. An instrument, comprising:
(a) a body;
(b) a shaft extending from the body; and
(c) an end effector in communication with the shaft, wherein the end effector is operable to compress, staple, and cut tissue, wherein the end effector comprises:
  (i) first and second opposing jaws, wherein at least one of the first and second jaws is movable relative to the other of the first and second jaws between an open configuration and a closed configuration,
  (ii) a staple assembly defining a longitudinal axis and configured to hold one or more staples, wherein the staple assembly is coupled with the second jaw, the staple assembly comprising:
    (A) a first lateral side,
    (B) a second lateral side disposed opposite the first lateral side, wherein the first and second lateral sides extend generally parallel to the longitudinal axis, and
    (C) a distal contact surface disposed between the first and second lateral sides, and
  (iii) a placement tip extending from a distal end of the first jaw or a distal end of the second jaw, wherein a curved portion of the placement tip extends along a curvilinear path relative to the longitudinal axis, wherein the curved portion extends laterally toward and beyond one of the first or second lateral sides, wherein the curved portion of the placement tip is configured to contact the opposing jaw in the closed position.

17. The instrument of claim 16, wherein the placement tip tapers along the entirety of the curved portion.

18. An instrument, comprising:
(a) a body;
(b) a shaft extending from the body; and
(c) an end effector in communication with the shaft, wherein the end effector defines a longitudinal axis, wherein the end effector is operable to compress, staple, and cut tissue, wherein the end effector comprises:
  (i) first and second opposing jaws, wherein at least one of the first and second jaws is movable relative to the other of the first and second jaws between an open position and a closed position, wherein one of the first and second jaws is configured to support a plurality of staples, and
  (ii) a placement tip extending from a distal end of the first jaw or a distal end of the second jaw, wherein the placement tip comprises:
    (A) a proximal portion having a proximal tip width, and
    (B) a distal portion having a distal tip width that is greater than a jaw width of the jaw disposed opposite the placement tip, wherein the distal portion is angled towards the opposite jaw and includes a first overhang portion that extends laterally away from and beyond a lateral side of the opposite jaw.

19. The instrument of claim 18, wherein the lateral side extends generally parallel to the longitudinal axis, wherein the jaw disposed opposite the placement tip extends distally past the distal portion.

* * * * *